US012799162B2

(12) United States Patent
Van de Water et al.

(10) Patent No.: US 12,799,162 B2
(45) Date of Patent: Nov. 17, 2026

(54) ANTIGENIC NEURON SPECIFIC ENOLASE PEPTIDES FOR DIAGNOSING AND TREATING AUTISM

(71) Applicant: THE REGENTS OF THE UNIVERSITY OF CALIFORNIA, Oakland, CA (US)

(72) Inventors: Judy Van de Water, Capay, CA (US); Elizabeth Edmiston, Sacramento, CA (US); Nora Alexandra Ramirez Celis, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1224 days.

(21) Appl. No.: 17/744,614

(22) Filed: May 13, 2022

(65) Prior Publication Data

US 2022/0324913 A1 Oct. 13, 2022

Related U.S. Application Data

(63) Continuation of application No. PCT/US2020/061969, filed on Nov. 24, 2020.

(60) Provisional application No. 62/940,175, filed on Nov. 25, 2019.

(51) Int. Cl.

| | |
|---|---|
| ***C07K 7/08*** | (2006.01) |
| ***A61K 39/00*** | (2006.01) |
| ***G01N 33/564*** | (2006.01) |
| ***G01N 33/68*** | (2006.01) |

(52) U.S. Cl.

CPC ............. *C07K 7/08* (2013.01); *G01N 33/564* (2013.01); *G01N 33/6893* (2013.01); *A61K 39/00* (2013.01); *G01N 2333/988* (2013.01); *G01N 2800/30* (2013.01); *G01N 2800/38* (2013.01)

(58) Field of Classification Search

CPC .... C07K 7/08; G01N 33/564; G01N 33/6893; G01N 2333/988; G01N 2800/30; G01N 2800/38; G01N 33/689; A61K 39/00; A61K 39/0007; C40B 40/10

See application file for complete search history.

(56) References Cited

U.S. PATENT DOCUMENTS

| | | | | |
|---|---|---|---|---|
| 4,833,092 | A | 5/1989 | Geysen | |
| 7,745,391 | B2 * | 6/2010 | Mintz | A61P 37/00 514/19.3 |
| 8,383,360 | B2 | 2/2013 | Van De Water et al. | |
| 10,428,124 | B2 * | 10/2019 | Sette | A61K 39/36 |
| 2005/0142616 | A1 | 6/2005 | Hanson | |
| 2015/0232539 | A1 | 8/2015 | Laird | |

FOREIGN PATENT DOCUMENTS

| | | | |
|---|---|---|---|
| CA | 2391568 | A1 | 12/2002 |
| JP | 2018531248 | A | 10/2018 |
| WO | 2004055519 | | 7/2004 |
| WO | 2006/091734 | A2 | 8/2006 |
| WO | 2008/012362 | A2 | 1/2008 |
| WO | 2011019929 | | 2/2011 |
| WO | 2015048332 | | 4/2015 |
| WO | 2016032977 | | 3/2016 |
| WO | 2016210137 | | 12/2016 |
| WO | WO-2017/062270 | A1 | 4/2017 |
| WO | WO-2017/176385 | A1 | 10/2017 |
| WO | 2017196432 | | 11/2017 |
| WO | 2021108379 | | 6/2021 |

OTHER PUBLICATIONS

Edmiston, Elizabeth et al., "Identification of the Antigenic Epitopes of Maternal Autoantibodies in Autism Spectrum Disorders", Brain Behav Immun., 69, Mar. 2018, pp. 399-407.

Braus, Barbara K., et al., Neuron-specific enolase antibodies in patients with sudden aquired retinal degeneration syndrome Vet. Immunol Immunopath, 2008,124, 177-83.

ISA/US, United States Patent and Trademark Office (USPTO), International Search Report and Written Opinion issued Apr. 26, 2021, related PCT international application No. PCT/US2020/061969, pp. 1-10, with claims searched, pp. 11-14.

Altschul et al., Basic local alignment search tool, J Mol Biol., 215(3):403-410 (Oct. 1990).

Altschul et al., Gapped BLAST and PSI-BLAST: a new generation of protein database search programs, Nucleic Acids Res., 25(17):3389-3402 (Sep. 1997).

Batzer et al., Enhanced evolutionary PCR using oligonucleotides with inosine at the 3'-terminus, Nucleic Acids Res., 19(18):5081 (Sep. 1991).

Burke et al., The Influence of Adjuvant on the Therapeutic Efficacy of a Recombinant Genital Herpes Vaccine, The Journal of Infectious Diseases, 170(5):1110-1119 (Nov. 1994).

Camarero et al., Biosynthesis of a Head-to-Tail Cyclized Protein with Improved Biological Activity, J. Am. Chem. Soc., 121(1):5597-5598 (1999).

Ed. Gupta et al., Autism Spectrum Disorders in Children, Pediatric Habilitation. Marcel Dekker, Inc., 12:1-337 (2004).

Geysen et al., Use of peptide synthesis to proper viral antigens for epitopes to a resolution of a single amino acid, Proc. Natl. Acad. Sci., 81:3998-4002 (Jul. 1984).

(Continued)

*Primary Examiner* — Olga N Chernyshev

(74) *Attorney, Agent, or Firm* — MARSHALL, GERSTEIN & BORUN LLP

(57) ABSTRACT

The present disclosure provides peptides that specifically bind to maternal autoantibodies that are generated in the mother or potential mother against the endogenous polypeptide antigen neuron specific enolase (NSE) protein. The peptides described herein are useful for determining a risk of an offspring for developing an autism spectrum disorder (ASD) by detecting the presence of maternal autoantibodies in a biological sample of the mother or potential mother. The peptides or mimotopes thereof can also be administered to the mother or potential mother to block the binding between maternal autoantibodies and their antigens, thereby neutralizing the maternal autoantibodies.

12 Claims, 8 Drawing Sheets

Specification includes a Sequence Listing.

(56) References Cited

OTHER PUBLICATIONS

Hecker et al., High-Density Peptide Microarray Analysis of IgG Autoantibody Reactivities in Serum and Cerebrospinal Fluid of Multiple Sclerosis Patients, Molecular & Cellular Proteomics, 15(4):1360-1380 (2016).
International Application No. PCT/US2020/061969, International Preliminary Report on Patentability, mailed Jun. 9, 2022.
International Application No. PCT/US2020/061969, Invitation to Pay Additional Fees, mailed Mar. 1, 2021.
Kessel et al., Multimerization of Peptide Mimotopes for Blocking of Factor VIII Neutralizing Antibodies, Chem Med Chem., 4(8):1364-1370 (Aug. 2009).
Knittelfelder et al., Mimotope vaccination—from allergy to cancer, Expert Opin Biol Ther., 9(4):493-506 (Apr. 2009).
Ohtsuka et al., An alternative approach to deoxyoligonucleotides as hybridization probes by insertion of deoxyinosine at ambiguous codon positions, J. Biol. Chem., 260(5):2605-2608 (Mar. 1985).
Ozonoff et al., From Kanner to the millennium: Scientific advances that have shaped clinical practice. In S. Ozonoff, S. J. Rogers, & R. L. Hendren (Eds.), Autism spectrum disorders: A research review for practitioners (pp. 3-33)., American Psychiatric Publishing, Inc., (2003).
Romanovskis et al., Preparation of head-to-tail cyclic peptides via side-chain attachment: Implications for library synthesis, The Journal of Peptide Research, 52(5):356-374 (Nov. 1998).
Rossolini et al., Use of deoxyinosine-containing primers vs degenerate primers for polymerase chain reaction based on ambiguous sequence information, Mol Cell Probes., 8(2):91-98 (Apr. 1994).
Sharav et al., Mimotope vaccines for cancer immunotherapy, Vaccine, 25(16):3032-3037 (Apr. 2007).
Tam et al., A biomimetic strategy in the synthesis and fragmentation of cyclic protein, Protein Science, 7(7):1583-1592 (Jul. 1998).
Tigges et al., Human herpes simplex virus (HSV)-specific CD8+ CTL clones recognize HSV-2-infected fibroblasts after treatment with IFN-gamma or when virion host shutoff functions are disabled, The Journal of immunology, 156 (10):3901-3910 (May 1996).
Valero et al., A comparative study of cyclization strategies applied to the synthesis of head-to-tail cyclic analogs of a viral epitope, The Journal of Peptide Research, 53(1):56-67 (Jan. 1999).
Yip et al., Epitope Discovery Using Monoclonal Antibodies and Phage Peptide Libraries, Comb Chem High Throughput Screen, 2(3):125-128 (1999).
Wang et al., Hypermethylation of the enolase gene (ENO2) in autism, Eur. J. Pediatr., 173: 1233-1244 (2014).
Edmiston et al., Identification of the antigenic epitopes of maternal autoantibodies in autism spectrum disorders, Brain Behav. Immun., 69: 399-407 (2018).
Bolandparvaz et al., Towards a nanoparticle-based prophylactic for maternal autoantibody-related autism, Nanomed.: NBM, 21: 102067 (2019).
Braunschweig, Daniel, et al., "Behavioral Correlates of Maternal Antibody Status Among Children with Autism", J. Autism Development Discord, vol. 42, Oct. 20, 2011, pp. 1435-1445.
Edmiston, Elizabeth, et al., "Autoimmunity, Autoantibodies, and Autism Spectrum Disorder", Biological Psychiatry, vol. 81, Mar. 1, 2017, pp. 383-390.
Zimmerman, Andrew H., et al., "Maternal antibrain antibodies in autism", Science Direct, Brain, Behavior and Immunity, vol. 21, 2007, pp. 351-357.
Braunschweig, Daniel, et al., "Autism: Maternally derived antibodies specific for fetal brain proteins", Science Direct, Neuro Toxicology, vol. 29, 2008, pp. 226-231.
Ali, Naael H., et al., "Maternal antineuronal antibodies and risk of childhood autism spectrum disorders: A case-control study", Science Direct, Journal of Chinese Medical Association, vol. 79, 2016, pp. 661-664.
Bolandparvaz, Amir, et al., "Towards a nanoparticle-based prophylactic for maternal autoantibody-related autism", Nanomedicine: Nanotechnology, Biology and Medicine, vol. 21, 2019, pp. 1-13.
Jones, Karen L., et al., "Maternal autoantibody related autism: mechanisms and pathways", Molecular Psychiatry, vol. 24, 2019, pp. 252-265.
European Patent Office (EPO), Communication (Extended European Search Report), issued Nov. 24, 2023, related European patent application No. 20892395.3, pp. 1-18, with claims searched pp. 19-22.
Canadian Intellectual Property Office, office action issued Mar. 20, 2024, related Canadian patent application No. 3,160,106, pp. 1-6, claims examined, pp. 7-14.
Canadian Intellectual Property Office, first office action issued Oct. 4, 2023, related Canadian patent application No. 3,160,106, pp. 1-4, claims examined, pp. 5-8.
Braunschweig et al., Autism-specific maternal autoantibodies recognize critical proteins in developing brain, Transl. Psychiatry, 3(7): e277 (Jul. 2013).
Maruyama et al., Autoantibody against neuron-specific enolase found in glaucoma patients causes retinal dysfunction in vivo, JP J. Ophthalmol., 46(1): 1-12 (Jan.-Feb. 2002).

* cited by examiner

SEQUENCE LISTING

<160> NUMBER OF SEQ ID NOS: 43

<210> SEQ ID NO 1
<211> LENGTH: 15
<212> TYPE: PRT
<213> ORGANISM: Homo sapiens

<400> SEQUENCE: 1

Asp Val Ala Ala Ser Glu Phe Tyr Arg Asp Gly Lys Tyr Asp Leu
1 5 10 15

<210> SEQ ID NO 2
<211> LENGTH: 15
<212> TYPE: PRT
<213> ORGANISM: Homo sapiens

<400> SEQUENCE: 2

Ile Glu Asp Pro Phe Asp Gln Asp Asp Trp Ala Ala Trp Ser Lys
1 5 10 15

<210> SEQ ID NO 3
<211> LENGTH: 15
<212> TYPE: PRT
<213> ORGANISM: Homo sapiens

<400> SEQUENCE: 3

Glu Arg Leu Ala Lys Tyr Asn Gln Leu Met Arg Ile Glu Glu Glu
1 5 10 15

<210> SEQ ID NO 4
<211> LENGTH: 15
<212> TYPE: PRT
<213> ORGANISM: Homo sapiens

<400> SEQUENCE: 4

Arg Leu Ala Lys Tyr Asn Gln Leu Met Arg Ile Glu Glu Glu Leu
1 5 10 15

<210> SEQ ID NO 5
<211> LENGTH: 19
<212> TYPE: PRT
<213> ORGANISM: Homo sapiens

<400> SEQUENCE: 5

Asp Tyr Pro Val Val Ser Ile Glu Asp Pro Phe Asp Gln Asp Asp Trp
1 5 10 15

Ala Ala Trp

<210> SEQ ID NO 6
<211> LENGTH: 15
<212> TYPE: PRT
<213> ORGANISM: Homo sapiens

<400> SEQUENCE: 6

Ser Glu Arg Leu Ala Lys Tyr Asn Gln Leu Met Arg Ile Glu Glu
1 5 10 15

<210> SEQ ID NO 7
<211> LENGTH: 15
<212> TYPE: PRT
<213> ORGANISM: Homo sapiens

<400> SEQUENCE: 7

Asp Tyr Pro Val Val Ser Ile Glu Asp Pro Phe Asp Gln Asp Asp
1 5 10 15

<210> SEQ ID NO 8
<211> LENGTH: 15
<212> TYPE: PRT
<213> ORGANISM: Homo sapiens

<400> SEQUENCE: 8

Tyr Pro Val Val Ser Ile Glu Asp Pro Phe Asp Gln Asp Asp Trp
1 5 10 15

<210> SEQ ID NO 9
<211> LENGTH: 15
<212> TYPE: PRT
<213> ORGANISM: Homo sapiens

<400> SEQUENCE: 9

Pro Val Val Ser Ile Glu Asp Pro Phe Asp Gln Asp Asp Trp Ala
1 5 10 15

<210> SEQ ID NO 10
<211> LENGTH: 15
<212> TYPE: PRT
<213> ORGANISM: Homo sapiens

<400> SEQUENCE: 10

Val Val Ser Ile Glu Asp Pro Phe Asp Gln Asp Asp Trp Ala Ala
1 5 10 15

<210> SEQ ID NO 11
<211> LENGTH: 15
<212> TYPE: PRT
<213> ORGANISM: Homo sapiens

<400> SEQUENCE: 11

Val Ser Ile Glu Asp Pro Phe Asp Gln Asp Asp Trp Ala Ala Trp
1 5 10 15

<210> SEQ ID NO 12
<211> LENGTH: 15
<212> TYPE: PRT
<213> ORGANISM: Homo sapiens

<400> SEQUENCE: 12

Gly Gly Phe Ala Pro Asn Ile Leu Glu Asn Ser Glu Ala Leu Glu
1 5 10 15

<210> SEQ ID NO 13
<211> LENGTH: 15
<212> TYPE: PRT
<213> ORGANISM: Homo sapiens

<400> SEQUENCE: 13

Thr Gly Asp Gln Leu Gly Ala Leu Tyr Gln Asp Phe Val Arg Asp
1 5 10 15

<210> SEQ ID NO 14
<211> LENGTH: 15
<212> TYPE: PRT
<213> ORGANISM: Homo sapiens

<400> SEQUENCE: 14

Gly Asp Gln Leu Gly Ala Leu Tyr Gln Asp Phe Val Arg Asp Tyr
1 5 10 15

<210> SEQ ID NO 15
<211> LENGTH: 15
<212> TYPE: PRT
<213> ORGANISM: Homo sapiens

<400> SEQUENCE: 15

Asp Gln Leu Gly Ala Leu Tyr Gln Asp Phe Val Arg Asp Tyr Pro
1 5 10 15

<210> SEQ ID NO 16
<211> LENGTH: 15
<212> TYPE: PRT
<213> ORGANISM: Homo sapiens

<400> SEQUENCE: 16

Asp Phe Val Arg Asp Tyr Pro Val Val Ser Ile Glu Asp Pro Phe
1 5 10 15

<210> SEQ ID NO 17
<211> LENGTH: 15
<212> TYPE: PRT
<213> ORGANISM: Homo sapiens

<400> SEQUENCE: 17

Ser Ile Glu Asp Pro Phe Asp Gln Asp Asp Trp Ala Ala Trp Ser
1 5 10 15

<210> SEQ ID NO 18

<211> LENGTH: 15
<212> TYPE: PRT
<213> ORGANISM: Homo sapiens

<400> SEQUENCE: 18

Arg Ser Glu Arg Leu Ala Lys Tyr Asn Gln Leu Met Arg Ile Glu
1 5 10 15

<210> SEQ ID NO 19
<211> LENGTH: 15
<212> TYPE: PRT
<213> ORGANISM: Homo sapiens

<400> SEQUENCE: 19

Leu Ala Lys Tyr Asn Gln Leu Met Arg Ile Glu Glu Glu Leu Gly
1 5 10 15

<210> SEQ ID NO 20
<211> LENGTH: 15
<212> TYPE: PRT
<213> ORGANISM: Homo sapiens

<400> SEQUENCE: 20

Ala Lys Tyr Asn Gln Leu Met Arg Ile Glu Glu Glu Leu Gly Asp
1 5 10 15

<210> SEQ ID NO 21
<211> LENGTH: 15
<212> TYPE: PRT
<213> ORGANISM: Homo sapiens

<400> SEQUENCE: 21

Lys Tyr Asn Gln Leu Met Arg Ile Glu Glu Glu Leu Gly Asp Glu
1 5 10 15

<210> SEQ ID NO 22
<211> LENGTH: 15
<212> TYPE: PRT
<213> ORGANISM: Homo sapiens

<400> SEQUENCE: 22

Gln Leu Met Arg Ile Glu Glu Glu Leu Gly Asp Glu Ala Arg Phe
1 5 10 15

<210> SEQ ID NO 23
<211> LENGTH: 15
<212> TYPE: PRT
<213> ORGANISM: Homo sapiens

<400> SEQUENCE: 23

Gln Asp Phe Val Arg Asp Tyr Pro Val Val Ser Ile Glu Asp Pro
1 5 10 15

<210> SEQ ID NO 24
<211> LENGTH: 15
<212> TYPE: PRT
<213> ORGANISM: Homo sapiens

<400> SEQUENCE: 24

Phe Val Arg Asp Tyr Pro Val Val Ser Ile Glu Asp Pro Phe Asp
1 5 10 15

<210> SEQ ID NO 25
<211> LENGTH: 15
<212> TYPE: PRT

<213> ORGANISM: Homo sapiens

<400> SEQUENCE: 25

Val Arg Asp Tyr Pro Val Val Ser Ile Glu Asp Pro Phe Asp Gln
1 5 10 15

<210> SEQ ID NO 26
<211> LENGTH: 15
<212> TYPE: PRT
<213> ORGANISM: Homo sapiens

<400> SEQUENCE: 26

Arg Asp Tyr Pro Val Val Ser Ile Glu Asp Pro Phe Asp Gln Asp
1 5 10 15

<210> SEQ ID NO 27
<211> LENGTH: 10
<212> TYPE: PRT
<213> ORGANISM: Influenza A virus

<400> SEQUENCE: 27

Tyr Pro Tyr Asp Val Pro Asp Tyr Ala Gly
1 5 10

<210> SEQ ID NO 28
<211> LENGTH: 14
<212> TYPE: PRT
<213> ORGANISM: Unknown
<220> FEATURE:
<223> OTHER INFORMATION: Description of Unknown:
Polio vaccine sequence

<400> SEQUENCE: 28

Lys Glu Val Pro Ala Leu Thr Ala Val Glu Thr Gly Ala Thr
1 5 10

<210> SEQ ID NO 29
<211> LENGTH: 15
<212> TYPE: PRT
<213> ORGANISM: Homo sapiens

<400> SEQUENCE: 29

Arg Tyr Ile Thr Gly Asp Gln Leu Gly Ala Leu Tyr Gln Asp Phe
1 5 10 15

<210> SEQ ID NO 30
<211> LENGTH: 15
<212> TYPE: PRT
<213> ORGANISM: Homo sapiens

<400> SEQUENCE: 30

Gln Leu Gly Ala Leu Tyr Gln Asp Phe Val Arg Asp Tyr Pro Val
1 5 10 15

<210> SEQ ID NO 31
<211> LENGTH: 15
<212> TYPE: PRT
<213> ORGANISM: Homo sapiens

<400> SEQUENCE: 31

Leu Tyr Gln Asp Phe Val Arg Asp Tyr Pro Val Val Ser Ile Glu
1 5 10 15

<210> SEQ ID NO 32
<211> LENGTH: 15

<212> TYPE: PRT
<213> ORGANISM: Homo sapiens

<400> SEQUENCE: 32

Tyr Gln Asp Phe Val Arg Asp Tyr Pro Val Val Ser Ile Glu Asp
1 5 10 15

<210> SEQ ID NO 33
<211> LENGTH: 15
<212> TYPE: PRT
<213> ORGANISM: Homo sapiens

<400> SEQUENCE: 33

Glu Asn Gly Trp Gly Val Met Val Ser His Arg Ser Gly Glu Thr
1 5 10 15

<210> SEQ ID NO 34
<211> LENGTH: 15
<212> TYPE: PRT
<213> ORGANISM: Homo sapiens

<400> SEQUENCE: 34

Asn Gly Trp Gly Val Met Val Ser His Arg Ser Gly Glu Thr Glu
1 5 10 15

<210> SEQ ID NO 35
<211> LENGTH: 15
<212> TYPE: PRT
<213> ORGANISM: Homo sapiens

<400> SEQUENCE: 35

Gly Trp Gly Val Met Val Ser His Arg Ser Gly Glu Thr Glu Asp
1 5 10 15

<210> SEQ ID NO 36
<211> LENGTH: 15
<212> TYPE: PRT
<213> ORGANISM: Homo sapiens

<400> SEQUENCE: 36

Tyr Asn Gln Leu Met Arg Ile Glu Glu Glu Leu Gly Asp Glu Ala
1 5 10 15

<210> SEQ ID NO 37
<211> LENGTH: 15
<212> TYPE: PRT
<213> ORGANISM: Homo sapiens

<400> SEQUENCE: 37

Asn Gln Leu Met Arg Ile Glu Glu Glu Leu Gly Asp Glu Ala Arg
1 5 10 15

<210> SEQ ID NO 38
<211> LENGTH: 15
<212> TYPE: PRT
<213> ORGANISM: Homo sapiens

<400> SEQUENCE: 38

Leu Met Arg Ile Glu Glu Glu Leu Gly Asp Glu Ala Arg Phe Ala
1 5 10 15

<210> SEQ ID NO 39
<211> LENGTH: 15
<212> TYPE: PRT
<213> ORGANISM: Homo sapiens

```
<400> SEQUENCE: 39

Met Arg Ile Glu Glu Glu Leu Gly Asp Glu Ala Arg Phe Ala Gly
1               5                   10                  15


<210> SEQ ID NO 40
<211> LENGTH: 15
<212> TYPE: PRT
<213> ORGANISM: Homo sapiens

<400> SEQUENCE: 40

Arg Ile Glu Glu Glu Leu Gly Asp Glu Ala Arg Phe Ala Gly His
1               5                   10                  15


<210> SEQ ID NO 41
<211> LENGTH: 15
<212> TYPE: PRT
<213> ORGANISM: Homo sapiens

<400> SEQUENCE: 41

Ile Glu Glu Glu Leu Gly Asp Glu Ala Arg Phe Ala Gly His Asn
1               5                   10                  15


<210> SEQ ID NO 42
<211> LENGTH: 15
<212> TYPE: PRT
<213> ORGANISM: Homo sapiens

<400> SEQUENCE: 42

Glu Glu Glu Leu Gly Asp Glu Ala Arg Phe Ala Gly His Asn Phe
1               5                   10                  15


<210> SEQ ID NO 43
<211> LENGTH: 15
<212> TYPE: PRT
<213> ORGANISM: Homo sapiens

<400> SEQUENCE: 43

Glu Glu Leu Gly Asp Glu Ala Arg Phe Ala Gly His Asn Phe Arg
1               5                   10                  15
```

ANTIGENIC NEURON SPECIFIC ENOLASE PEPTIDES FOR DIAGNOSING AND TREATING AUTISM

CROSS-REFERENCE TO RELATED APPLICATIONS

This application claims priority to, and is a 35 U.S.C. § 111(a) continuation of, PCT international application number PCT/US2020/061969 filed on Nov. 24, 2020, incorporated herein by reference in its entirety, which claims priority to, and the benefit of, U.S. provisional patent application Ser. No. 62/940,175 filed on Nov. 25, 2019, incorporated herein by reference in its entirety. Priority is claimed to each of the foregoing applications.

The above-referenced PCT international application was published as PCT International Publication No. WO 2021/108379 A1 on Jun. 3, 2021, which publication is incorporated herein by reference in its entirety.

STATEMENT REGARDING FEDERALLY SPONSORED RESEARCH OR DEVELOPMENT

This invention was made with Government support under Grant No. 2P01ES011269-11 awarded by the National Institutes of Health (NIH). The Government has certain rights in the invention.

INCORPORATION-BY-REFERENCE OF SEQUENCE LISTING

This application includes a sequence listing in a text file entitled "UC-2018-806-2-US-sequence-listing.txt" created on Apr. 19, 2022 and having a 9 kb file size. The sequence listing is submitted through EFS-Web and is incorporated herein by reference in its entirety.

BACKGROUND

Autism spectrum disorders (ASD) are a set of neurodevelopmental disorders diagnosed in early childhood and are classified by a loss of abilities in social interaction, social communication, and the presence of repetitive and restricted interests and behaviors. In 2018, the CDC estimated that 1 in 59 children are affected in the USA, making ASD an important health concern and a substantial socioeconomic burden for affected families and the healthcare system. Current therapeutic interventions available for ASD are behaviorally directed or symptom-based pharmacological treatments applied only after diagnosis. Little is known about the cause of ASD and while certain therapeutic approaches applied following early diagnosis have shown promise, no preventive alternatives exist currently.

What is known is that activation of the maternal immune system during early fetal growth can have a negative effect on brain development. For reasons that are not clear, the immune system in some pregnant women produces autoantibodies (proteins produced by the immune system in response to a constituent of one's own tissues) that mistakenly identify parts of the fetal brain as foreign substances. As a result, gestational exposure to these maternal autoantibodies could lead to alterations in neurodevelopment characteristic of ASD. Indeed, 23% of mothers who gave birth to children with ASD have circulating autoantibodies against seven proteins highly expressed in the developing brain, in contrast to only 1% of mothers that deliver otherwise normal children. Each of the proteins is known to play an important role in neurodevelopment; interference with the level or function of more than one of them could act synergistically to change the trajectory of brain development. See, U.S. Pat. No. 8,383,360.

As such, there is a need for early, non-genetic, epitope-specific biomarkers to determine the maternal risk of having a child with ASD. There is also a compelling need to address the cause and treatment of ASD, and not just the associated symptoms, by creating highly specific therapeutics and/or intervention tools. Early identification of these maternal autoantibodies in the affected mother would allow for early medical interventions to limit fetal exposure to autoantibodies and the consequent risk of her child developing ASD, thereby reducing the prevalence of ASD and improving the quality of life for otherwise affected children and their families. The present disclosure satisfies these needs and provides related advantages as well.

SUMMARY

The present disclosure provides peptides (e.g., peptide epitopes) that specifically bind to maternal autoantibodies that are generated in the mother or potential mother against a neuron specific enolase (NSE) polypeptide. The peptides described herein are useful for determining a risk of an offspring for developing an autism spectrum disorder (ASD) by detecting the presence of maternal autoantibodies in a biological sample of the mother or potential mother. The peptides can also be administered to the mother or potential mother to block the binding between maternal autoantibodies and their antigens, thereby neutralizing the maternal autoantibodies. Furthermore, the peptides can be utilized in immunoadsorption to remove circulating autoantibodies from maternal plasma.

In a first aspect, provided herein is an isolated peptide having at least about 80% sequence identity to any one of SEQ ID NOS:1-6. In some embodiments, the peptide comprises at least 5, 6, 7, 8, 9, 10, 11, 12, 13, 14, or 15 contiguous amino acids of any one of SEQ ID NOS:1-6. In some embodiments, the peptide binds to a maternal antibody that binds to a neuron specific enolase (NSE) protein.

In some embodiments, the peptide is from about 15 to about 30 amino acids in length. In some embodiments, the peptide is up to about 25 amino acids in length. In particular embodiments, the peptide comprises an amino acid sequence consisting of any one of SEQ ID NOS:1-6.

In some embodiments, the peptide is a mimotope. In some embodiments, the mimotope comprises D-amino acids. In other embodiments, the mimotope comprises one or more amino acid modifications (e.g., substitutions) relative to any one of SEQ ID NOS:1-6.

In some embodiments, the peptide further comprises a label, e.g., biotin, a fluorescent label, a chemiluminescent label, and a radioactive label. In other embodiments, the label is attached (e.g., covalently attached) to the peptide.

In another aspect, the disclosure provides a composition comprising a peptide described herein or a plurality thereof. In some embodiments, the composition further comprises a pharmaceutically acceptable carrier. In particular embodiments, the peptide or plurality thereof in the composition is selected from the group consisting of SEQ ID NOS:1-6. In particular embodiments, the plurality of peptides comprises at least 2, 3, 4, 5, or 6 different peptides. In some embodiments, the different peptides bind to the same maternal antibodies, e.g., an antibody against NSE.

In another aspect, the disclosure provides a kit comprising a peptide described herein or a plurality thereof and a solid support. In some embodiments, the solid support is a multiwell plate, an ELISA plate, a microarray, a chip, a bead, a porous strip, or a nitrocellulose filter. In some embodiments, the peptide or plurality thereof is immobilized on (e.g., covalently attached to) the solid support. In particular embodiments, the peptide or plurality thereof is selected from the group consisting of SEQ ID NOS:1-6. In particular embodiments, the plurality of peptides comprises at least 2, 3, 4, 5, or 6 different peptides. In some embodiments, the different peptides bind to the same maternal antibodies, e.g., an antibody against NSE.

In some embodiments, the kit further comprises instructions for use. In some instances, the instructions for use include instructions for contacting the solid support with a biological sample from the mother or potential mother. In other instances, the instructions for use include instructions for correlating the presence of maternal antibodies that bind to one or more peptides with an increased risk of an offspring (e.g., fetus or child) at developing an ASD. In other embodiments, the kit further comprises labeled secondary antibodies for detecting the presence of maternal antibodies that bind to one or more peptides.

In other embodiments, the kit further comprises negative and positive control samples. In some instances, the negative control samples are obtained from mothers who have typically developing (TD) children. In other instances, the biological sample and/or the control samples are reactive to full-length NSE. In yet other instances, neither the biological nor the control samples is reactive to full-length NSE. In further embodiments, the kit further comprises a secondary antibody labeled directly or indirectly with a detectable moiety.

In another aspect, the disclosure provides a method for determining a risk of an offspring for developing an autism spectrum disorder (ASD), the method comprising: detecting in a biological sample from the mother or potential mother of the offspring the presence or absence of maternal antibodies that bind to a peptide described herein or a plurality thereof, wherein the presence of maternal antibodies that bind to the peptide or plurality thereof indicates an increased risk of the offspring for developing an ASD.

In some embodiments of the method, the method further comprises obtaining a sample from the mother or potential mother. In certain embodiments, the sample is selected from the group consisting of blood, serum, plasma, amniotic fluid, breast milk, and saliva. In some embodiments, the peptide or plurality thereof is selected from the group consisting of SEQ ID NOS:1-6. In some embodiments of the method, the plurality of peptides comprises at least 2, 3, 4, 5, or 6 different peptides. In particular embodiments, the different peptides bind to the same maternal antibodies, e.g., an antibody against NSE. In some embodiments of the method, the peptide or plurality thereof is attached to a solid support, e.g., a multiwell plate, an ELISA plate, a microarray, a chip, a bead, a porous strip, or a nitrocellulose filter.

In some embodiments of the method, the maternal antibodies are detected by a technique such as, e.g., Western blot, dot blot, ELISA, radioimmunoassay, immunoprecipitation, electrochemiluminescence, immunofluorescence, FACS analysis, or multiplex bead assay.

In some embodiments of the method, the presence of maternal antibodies in a test sample (i.e., a biological sample from the mother or potential mother) is detected without comparing the test sample to a control sample. In other embodiments, the test sample is compared to a positive or negative control sample. In some instances, the test sample and/or the control sample is reactive to full-length NSE. In other instances, neither the test sample nor the control sample is reactive to full-length NSE. In yet other instances, the negative control is obtained from a mother who has TD children.

In some embodiments of the method, the mother or potential mother has a child with an ASD. In some embodiments, the mother or potential mother has a familial history of ASD or autoimmune disease.

In another aspect, the disclosure provides a method for preventing or reducing a risk of an offspring for developing an autism spectrum disorder (ASD), the method comprising: administering a therapeutically effective amount of a peptide described herein or a plurality thereof to the mother or potential mother of the offspring, wherein the peptide or plurality thereof binds to maternal antibodies circulating in the mother or potential mother to form neutralizing complexes, thereby preventing or reducing the risk of the offspring for developing an ASD.

In some embodiments of the method, the method further comprises removing the neutralizing complexes from the mother or potential mother. In some embodiments of the method, the neutralizing complexes are removed by affinity plasmapheresis.

In some embodiments of the method, the peptide or plurality thereof is administered intravenously. In some embodiments, the peptide or plurality thereof is selected from the group consisting of SEQ ID NOS:1-6. In particular embodiments, the plurality of peptides comprises at least 2, 3, 4, 5, or 6 different peptides. In some embodiments, the different peptides bind to the same maternal antibodies, e.g., an antibody against NSE.

Other objects, features, and advantages of the present disclosure will be apparent to one of skill in the art from the following detailed description.

BRIEF DESCRIPTION OF THE DRAWINGS

(FIG. 1A) Ponceau stained nitrocellulose membrane containing samples from the first fraction, and every tenth fraction thereafter, collected from the Prep Cell separation of FMB. (FIG. 1B) WB of the duplicated membrane shown in FIG. 1A probed with a pool of maternal plasma reactive to 37 kDa (LDH), 39 kDa (YBX1), 44 kDa (GDA), and 73 kDa (STIP1, CRMP1/2) antigens. (FIG. 1C) Prep Cell fractions, which contained proteins between 39-42 kDa. Fraction #12 was used for 2D gel electrophoresis. (FIG. 1D) WB of FMB fraction #12 probed with maternal plasma not reactive to LDHA-B, GDA and YBX1. Lane 1: secondary-only antibody control, Lanes 2-4: maternal plasma reactive to LDHA-B (Green Arrows), YBX1 (Blue Arrows), and GDA (Black Arrow). Lanes 5-8: maternal plasma pool #1 and with band reactivity to a protein near 39 kDa. Lanes 10-14: maternal plasma pool #2 with band reactivity to two proteins near 37 and 39 kDa. Lane 9: plasma sample negative-control to FMB antigens. Abbreviations: FMB, fetal monkey brain; LDH A and B, lactate dehydrogenase A and B; YBX1, Y-box binding protein 1; GDA, guanine deaminase; CRMP1 and CRMP2, collapsin response mediator 1 and 2; and STIP1, stress induced phosphoprotein 1.

FIG. 2A depicts anti-IgG stained gel for protein alignment with FMB fraction #12 (FIG. 2B) and the membraned blotted with plasma pool 1 and plasma pool 2 (FIG. 2C). FIG. 2D depicts the merged images of FIG. 2B and FIG. 2C. (FIG. 2E) WB of the proteins that were bound by maternal IgG antibodies (Pooled plasma 1 and 2), each of which was labeled with a spot number. In total, 27 protein spots were picked and subsequently analyzed by mass spectrometry.

DETAILED DESCRIPTION

I. Introduction

Figure 1A:
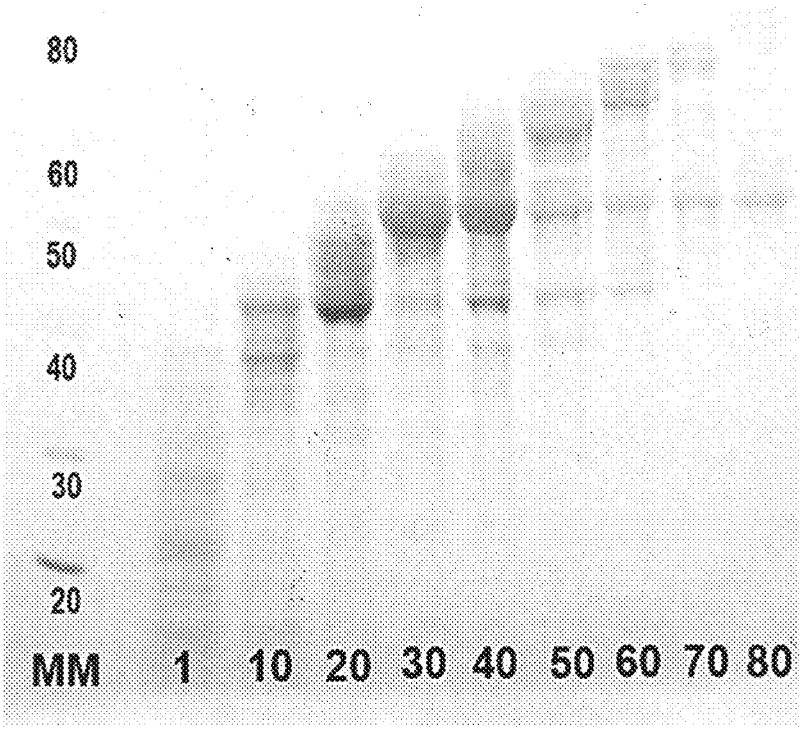
FIGS. 1A-1D. Western blot (WB) of fetal monkey brain (FMB) probed with maternal plasma.
Figure 1B:
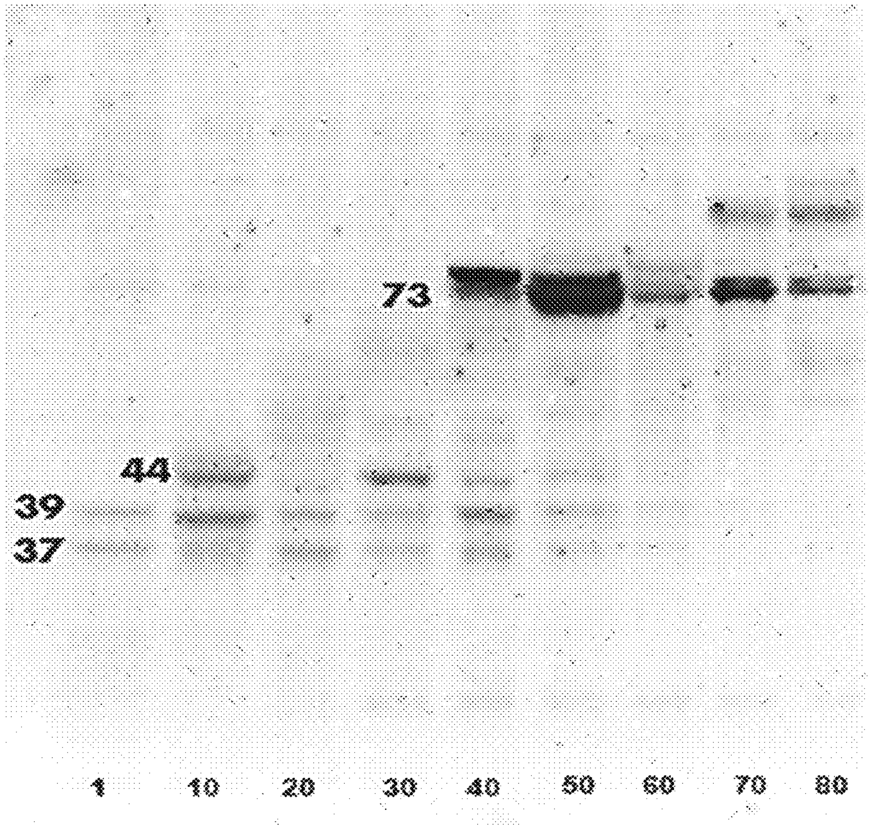
Figure 1C:
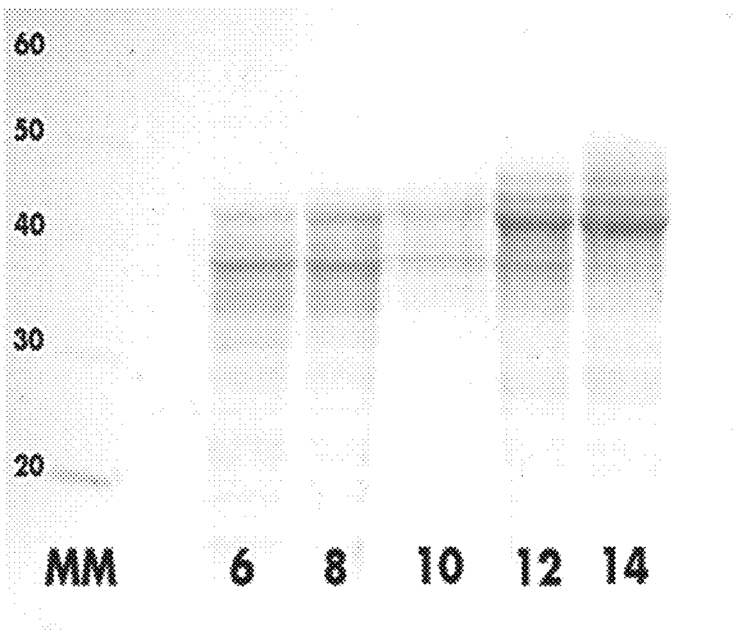

Autism spectrum disorder (ASD) is an important health issue characterized by social and behavioral impairments, along with restricted interests and repetitive behaviors. Prior studies determined that maternal autoantibody-related (MAR) autism is thought to be associated with about 23% of ASD cases. Seven MAR-specific autoantigens including CRMP1, CRMP2, GDA, LDHA, LDHB, STIP1, and YBX1 were identified previously, see, e.g., International Patent Publication No. WO 2016/210137, which is incorporated by reference herein in its entirety. The epitope peptide sequences recognized by maternal autoantibodies for each of the seven ASD-specific autoantigens were also described.

The present disclosure is directed to additional antigens recognized by the ASD-specific maternal autoantibodies, as well as to the mapping of the unique ASD-specific epitopes using microarray technology. Fetal Rhesus macaque brain tissues were separated by molecular weight and a fraction containing bands between 37 and 45 kDa was analyzed using 2-D gel electrophoresis, followed by peptide mass mapping using MALDI-TOF MS and TOF/TOF tandem MS/MS. Using this methodology, neuron specific enolase (NSE) was identified as a target autoantigen and selected for epitope mapping. The full NSE sequence was translated into 15-mer peptides with an overlap of 14 amino acids onto microarray slides and probed with maternal plasma from mothers with an ASD child and from mothers with a Typically Developing child (TD) (ASD=27 and TD=21). The resulting data were analyzed by T-test. 16 ASD-specific NSE-peptide sequences were found, for which four sequences were statistically significant (p<0.05), using both the t-test and SAM t-test: DVAASEFYRDGKYDL (SEQ ID NO:1) (SEQ ID NO:1) (p=0.047; SAM score 1.49), IEDPFDQDDWAAWSK (SEQ ID NO:2) (SEQ ID NO:2) (p=0.049; SAM score 1.49), ERLAKYNQLMRIEEE (SEQ ID NO:3) (SEQ ID NO:3) (p=0.045; SAM score 1.57), and RLAKYNQLMRIEEEL (SEQ ID NO:4) (p=0.017: SAM score 1.82). All ASD-specific NSE-peptide sequences had an odds ratio (OR) above 3, with SERLAKYNQLMRIEE (SEQ ID NO:6) (OR 10.1, CI 95% 0.5094 to 200.7) and ERLAKYNQLMRIEEE (SEQ ID NO:3) (OR 12.6, CI 95% 0.6408 to 247.7) being the two epitopes with the highest ORs. 5 sequences were found that were recognized by both ASD and TD antibodies, suggesting a large immunodominant epitope (DYPVVSIEDPFDQDDWAAW (SEQ ID NO:5)). While maternal autoantibodies against the NSE protein are present both in mothers with ASD and mothers of TD children, there are several ASD-specific epitopes that can potentially be used as MAR ASD biomarkers.

II. Definitions

As used herein, the following terms have the meanings ascribed to them unless specified otherwise.

The terms “autism spectrum disorder,” “autistic spectrum disorder,” “autism” or “ASD” refer to a spectrum of neurodevelopmental disorders characterized by impaired social interaction and communication accompanied by repetitive and stereotyped behavior. Autism includes a spectrum of impaired social interaction and communication, however, the disorder can be roughly categorized into “high functioning autism” or “low functioning autism,” depending on the extent of social interaction and communication impairment. Individuals diagnosed with “high functioning autism” have minimal but identifiable social interaction and communication impairments (i.e., Asperger’s syndrome). Additional information on autism spectrum disorders can be found in, for example, Autism Spectrum Disorders: A Research Review for Practitioners, Ozonoff, et al., eds., 2003, American Psychiatric Pub; Gupta, Autistic Spectrum Disorders in Children, 2004, Marcel Dekker Inc; Hollander, Autism Spectrum Disorders, 2003, Marcel Dekker Inc; Handbook of Autism and Developmental Disorders, Volkmar, ed., 2005, John Wiley; Sicile-Kira and Grandin, Autism Spectrum Disorders: The Complete Guide to Understanding Autism, Asperger’s Syndrome, Pervasive Developmental Disorder, and Other ASDs, 2004, Perigee Trade; and Duncan, et al., Autism Spectrum Disorders [Two Volumes]: A Handbook for Parents and Professionals, 2007, Praeger.

The terms “typically developing” and “TD” refer to a subject who has not been diagnosed with an autism spectrum disorder (ASD). Typically developing children do not exhibit the ASD-associated impaired communication abilities, impaired social interactions, or repetitive and/or stereotyped behaviors with a severity that is typically associated with a diagnosis of an ASD. While typically developing children may exhibit some behaviors that are displayed by children who have been diagnosed with an ASD, typically developing children do not display the constellation and/or severity of behaviors that supports a diagnosis of an ASD.

The term “isolated,” when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term “purified” denotes that a nucleic acid or protein gives rise to essentially one band in an electrophoretic gel. Particularly, it means that the nucleic acid or protein is at least 85% pure, at least 95% pure, or at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues, or an assembly of multiple polymers of amino acid residues. The terms apply to amino acid polymers in which one or more amino acid residue is an artificial chemical mimic of a corresponding naturally occurring amino acid, as well as to naturally occurring amino acid polymers and non-naturally occurring amino acid polymer.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gin), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an a carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins, 1993).

The term "amino acid modification" or "amino acid alteration" refers to a substitution, a deletion, or an insertion of one or more amino acids.

"Percentage of sequence identity" is determined by comparing two optimally aligned sequences over a comparison window, wherein the portion of the sequence (e.g., a peptide described herein) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more polypeptide or peptide sequences, refer to two or more sequences or subsequences that are the same sequences. Two sequences are "substantially identical" if two sequences have a specified percentage of amino acid residues that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information.

An indication that two polypeptide or peptide sequences are substantially identical occurs when a first polypeptide or peptide is immunologically cross-reactive with the antibodies raised against a second polypeptide or peptide. Thus, a first polypeptide or peptide is typically substantially identical to a second polypeptide or peptide, for example, where the two sequences differ only by conservative substitutions.

The term "antigenic fragment" refers to a contiguous subsequence of a polypeptide that binds to an antibody. An antigenic fragment may or may not be immunogenic, i.e., it may or may not induce an immune response.

The term "conformational antigenic fragment" refers to a spatially contiguous region of a polypeptide or tetramer which may or may not be formed by a contiguous subsequence. A conformational antigenic fragment may or may not be immunogenic.

The term "epitope" or "antigenic determinant" refers to a site on a peptide or polypeptide to which B and/or T cells respond. B cell epitopes can be formed both from contiguous amino acids or noncontiguous amino acids juxtaposed by tertiary or quaternary folding of a protein. Epitopes formed from contiguous amino acids are typically retained on exposure to denaturing solvents whereas epitopes formed by tertiary or quaternary folding (i.e., conformationally determined) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen (e.g., an electrochemiluminescence assay, a competitive ELISA, a solid phase radioimmunoassay (SPRIA) or a blocking Western blot). T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. (1996) 156:3901-3910) or by cytokine secretion.

The terms "bind(s) specifically" or "specifically directed against" refers to the preferential association between T cell receptors and/or antibodies, in whole or part, with a target peptide/polypeptide or an antigenic fragment thereof in comparison to other peptides/polypeptides. It is, of course, recognized that a certain degree of non-specific interaction may occur between an antibody or T cell receptor and a non-target peptide/polypeptide. Nevertheless, specific binding may be distinguished as mediated through specific recognition of the target peptide/polypeptide or an antigenic fragment thereof. Typically, specific binding or a specifically directed immune response results in a much stronger association between the target peptide/polypeptide and an antibody against the target peptide/polypeptide or T cell receptor than between an antibody against the target peptide/polypeptide or T cell receptor and a non-target peptide/polypeptide. Specific binding typically results in greater than about a 10-fold (e.g., greater than 100-fold) increase in the amount of bound antibody (per unit time) against the target peptide/polypeptide to a cell or tissue bearing the target peptide/polypeptide as compared to a cell or tissue lacking an epitope of the target peptide/polypeptide. Specific binding between the target peptide/polypeptide and an antibody against the target peptide/polypeptide generally means an affinity of at least $10^6$ $M^{-1}$. Affinities greater than $10^8$ $M^{-1}$ are preferred. Specific binding can be determined using any assay for antibody binding known in the art, including without limitation, Western blot, dot blot, ELISA, flow cytometry, electrochemiluminescence, multiplex bead assay (e.g., using Luminex or fluorescent microbeads), and immunohistochemistry. T cells specifically directed against an epitope of a target peptide/polypeptide typically exhibit antigen-induced proliferation in response to the target peptide/polypeptide that is greater than about 2-fold (e.g., greater than about 5-fold or 10-fold) than antigen-induced proliferation in response to a non-target peptide/polypeptide. T cell proliferation assays are known in the art and can be measured by $^3$H-thymidine incorporation.

The term "sample" refers to any biological specimen obtained from a subject, e.g., a human subject. Samples include, without limitation, whole blood, plasma, serum, red blood cells, white blood cells, saliva, urine, stool, sputum, bronchial lavage fluid, tears, nipple aspirate, breast milk, any other bodily fluid, a tissue sample such as a biopsy of a placenta, and cellular extracts thereof. In some embodiments, the sample is whole blood or a fractional component thereof, such as plasma, serum, or a cell pellet.

The term "subject," "individual," or "patient" typically includes humans, but can also include other animals such as, e.g., other primates, rodents, canines, felines, equines, ovines, porcines, and the like. In particular embodiments, the subject is a human subject.

The term "increased risk of developing an ASD" refers to an increased likelihood or probability that a fetus or child exposed to antibodies that bind to one or more antigens described herein (e.g., NSE) or to levels of antibodies against one or more of the antigens above a predetermined threshold level will develop symptoms of an ASD in comparison to the risk, likelihood or probability of a fetus or child that has not been exposed to antibodies against the one or more antigens or to levels of antibodies against the one or more antigens that are below a predetermined threshold level.

The term "reduced risk of developing an ASD" refers to the decreased likelihood or probability that a fetus or child exposed to antibodies against one or more antigens described herein (e.g., NSE) or to levels of antibodies against one or more of the antigens above a predetermined threshold level, and whose mother has received therapeutic intervention, e.g., to block, inactivate or remove antibodies that bind to the antigens, will develop symptoms of an ASD in comparison to the likelihood or probability that a fetus or child exposed to antibodies against the antigens or to levels of antibodies against the one or more antigens above a predetermined threshold level and whose mother has not received therapeutic intervention will develop symptoms of an ASD.

The term "peptide epitope" or "antigenic peptide" refers to peptides or fragments of one or more antigens described herein (e.g., NSE) that imitate an epitope (e.g., bound by an antibody against the antigen), although no clear homology may exist between the structure or sequence of such peptide epitopes and the epitope of the native antigen. Instead, mimicry of a peptide epitope relies on similarities in physicochemical properties and similar spatial organization. The screening and construction of peptide epitopes is known in the art. For example, peptide epitopes can be derived from known epitopes by sequence modification or developed de novo using combinatorial peptide libraries for peptides, e.g., that bind to antibodies against the one or more antigens. See, e.g., Yip and Ward, Comb Chem High Throughput Screen (1999) 2(3):125-128; Sharav, et al, Vaccine (2007) 25(16): 3032-37; and Knittelfelder, et al., Expert Opin Biol Then (2009) 9(4):493-506.

The term "familial history" refers to the presence of a disease condition (e.g., an ASD or an autoimmune disease) in a family member. The family member can be of direct lineage, e.g., a parent, a child or a grandparent or a close relation, e.g., a sibling, an aunt or uncle, a cousin. Typically, the family member is a blood relative with a common genetic heritage.

The term "therapeutically effective amount" refers to the amount of a peptide described herein that is capable of achieving a therapeutic effect or the desired result (i.e., a sufficient amount of peptide to block binding of antibodies against the antigen to the target antigen), preferably with minimal or no side-effects. In some embodiments, a therapeutically acceptable amount does not induce or cause undesirable side-effects. A therapeutically effective amount can be determined by first administering a low dose, and then incrementally increasing that dose until the desired effect is achieved. A "prophylactically effective amount" and a "therapeutically effective amount" of an antibody blocking agent described herein can prevent the onset of or result in a decrease in severity of an ASD. A "prophylactically effective amount" and a "therapeutically effective amount" can also prevent or ameliorate, respectively, impairment or disability due to the disorders and diseases resulting from the activity of maternal antibodies.

The term "pharmaceutically acceptable carrier" refers to a compound, chemical, or molecule that is useful in preparing a pharmaceutical composition that is generally safe, non-toxic, and neither biologically nor otherwise undesirable and includes that which is acceptable for pharmaceutical use in a subject. Suitable pharmaceutical carriers are described herein and in "Remington's Pharmaceutical Sciences" by E. W. Martin.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a peptide described herein for preventing or relieving one or more symptoms associated with the presence or activity of maternal antibodies. By "co-administer" it is meant that a peptide described herein is administered at the same time, just prior to, or just after the administration of a second drug.

As used herein, the term "treating" refers to any indicia of success in the treatment or amelioration of a pathology or condition, including any objective or subjective parameter such as abatement, remission, diminishing of symptoms or making the pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, histopathological examination (e.g., analysis of biopsied tissue), laboratory analysis of urine, saliva, tissue sample, serum, plasma, or blood, or imaging.

The term "specifically inhibit(s)" refers to the ability of an agent (e.g., a peptide described herein) to inhibit the binding of antibodies against one or more antigens (e.g., NSE). Specific inhibition typically results in at least about a 2-fold inhibition over background, for example, greater than about 10-fold, 20-fold, 50-fold inhibition of binding of antibodies against the target antigen, for example, by comparing the binding of the antibodies in the absence of the agent. In some embodiments, the binding of antibodies to the target antigen is completely inhibited or blocked by the agent (e.g., a peptide described herein). Typically, specific inhibition is a statistically meaningful reduction in antibody binding to the target antigen (e.g., $p<0.05$) using an appropriate statistical test.

The term "agent" includes peptides (e.g., peptide epitopes), mimotopes, polypeptides (e.g., ligands, antibodies), nucleic acids, small organic compounds, and the like.

The term "solid support" refers to any material suitable for performing the methods described herein, such as plastic or glass tubes, beads, slides, microtiter plates, porous filters or membranes, non-porous filters or membranes, nonmagnetic beads, microbeads, slides, microarrays, and the like.

The term "neutralizing complex" refers to a complex comprising a maternal antibody bound to a specific peptide described herein that prevents/inhibits/blocks the maternal antibody from binding to its antigen (e.g., NSE). For instance, a maternal autoantibody that specifically recognizes the NSE antigen can form a neutralizing complex with an NSE peptide described herein or mimotope thereof, such that the maternal autoantibody does not bind to the NSE antigen.

The term "affinity plasmapheresis" refers to an extracorporeal blood purification procedure for the removal of deleterious agents (e.g., disease-causing agents) from the plasma of a subject.

III. Detailed Description of the Embodiments

The present disclosure provides peptides (e.g., peptide epitopes and mimotopes thereof) that specifically bind to maternal autoantibodies against the endogenous autoantigen NSE protein. The present disclosure also provides compositions and kits comprising the peptides described herein. In addition, the present disclosure provides methods for determining a risk of a child or future offspring (e.g., in a mother or a potential mother who is pregnant or prior to conception) for developing an autism spectrum disorder (ASD) by detecting the presence of maternal autoantibodies in a biological sample of the mother or potential mother using the peptides described herein. The present disclosure further provides methods for preventing or reducing a risk of an offspring for developing an ASD by administering a therapeutically effective amount of the peptides described herein to the mother or potential mother of the offspring to block the binding between maternal autoantibodies and their antigens.

A. Neuron Specific Enolase (NSE)

NSE is one of the most abundant proteins in the brain and can account for 0.4-2.2% of total soluble protein depending on the brain region. It has been implicated as having different roles including those in the glycolysis and gluconeogenesis pathways, neural cell differentiation, activation, and proliferation through the PI3K/Akt and MAPK/ERK signaling pathways. Further, NSE plays a role in the activation of the RhoA kinase pathways that can result in neurodegeneration or neuroprotection depending on the strength of the signal. In addition, NSE has been shown to be involved in CNS inflammatory processes as its expression is upregulated in M1 microglia and reactive astrocytes. Therefore, NSE plays several important roles during neurodevelopment but has also been implicated in neurodegeneration [18].

Measurement of plasma NSE levels has been used as a biomarker for various applications [17]. For example, it is a useful indicator of neural maturation, and is currently the most widely used biomarker for small cell lung cancer (SCLC), and it has been shown to have a direct effect in cell growth and migration in vitro on different SCLC cell lines [28, 29]. Additionally, it is also used in the diagnosis and prognosis of other types of cancers such as non-small cell lung cancer (NSCLC), neuroendocrine tumors (NETs), neuroblastoma, brain cancer and brain injury (TBI) [30]. As described in the Examples herein, we addressed the value of autoantibodies to NSE as a potential biomarker or risk factor for MAR ASD based on the concept that antibody binding to NSE during neurogenesis could impact protein functionality and brain metabolism, having a lasting impact neuronal tissue functionality and development.

As described in the Examples herein, we found that autoantibody reactivity against NSE was present at similar rates for both experimental groups (ASD and TD). This indicates that the intact NSE protein is not a biomarker on its own, similar to previous studies demonstrating the necessity of autoantibody reactivity to multiple rather than single antigens to confer ASD specificity [8, 12, 13, 31, 32]. When we first discovered the original seven autoantigens, we found that reactivity to specific antigen combinations were highly significant as a biomarker of ASD risk, including LDH, STIP1 and CRMP1 (13% ASD vs 0% TD) and several other combinations of 3 or more autoantigens with >98% specificity [6, 8, 9]. We therefore tested NSE using a larger data set and found that it increases the specificity and sensitivity of a MAR ASD assay.

In a recent study, we performed microarray-based epitope mapping of CRMP1, CRMP2, GDA, LDHA/B, STIP1, and YBX1 and further described differential reactivity to several epitopes recognized only by autoantibodies from mothers of children with ASD [15]. Additionally, we used the epitopes from our original set of autoantigens to create an endogenous antigen-driven mouse model for autism, in which mice were immunized with peptide epitopes for LDHA, LDHB, CRMP1 and STIP1. This methodology allowed constant exposure of the embryos to autoantibodies against the MAR ASD specific peptides throughout gestation. Hence, we created a mouse model that displayed ASD-relevant behaviors, demonstrating that exposure to this combination of autoantibodies led to alterations in neurodevelopment [11].

As described in the Examples herein, we identified NSE as an additional MAR ASD autoantigen, and found 16 epitope sequences that are recognized by maternal autoantibodies present only in the ASD group, with 4 of those sequences demonstrating statistical significance when compared with the control group using traditional t-test and SAM score t-test analysis. Epitope Sequences (ES 408 and 409) SERLAKYNQLMRIEE (SEQ ID NO:6) and ERLAKYNQLMRIEEE (SEQ ID NO:3) had the greatest OR values (10.1 and 12.6, respectively) indicating a strong association between having autoantibodies against these sequences and risk of having a child with ASD. These ASD-specific epitope peptides can be used to create MAR ASD animal models that allow an evaluation of the impact of the NSE ASD-specific peptides individually and in combination with pathogenic epitopes from other autoantigens, thus providing a better understanding of the role of anti-NSE in autism pathology.

As a mechanism of action, we hypothesize that the presence of autoantibodies to the ASD-specific NSE epitopes could potentially inhibit proper protein function in two different ways: 1) by directly interfering with proper protein folding (tertiary and quaternary structure) or, 2) by binding critical functional sites (catalytic or substrate sites) [33-36]. While it is possible that anti-NSE antibodies in developing brain could elicit a response against cells targeted by these autoantibodies, we lack evidence of tissue destruction based on our previous rodent models. Instead, the presence of MAR ASD autoantibodies to CRMP1, LDHA/B, and STIP1 seems to affect progenitor cell maturation and alteration of adult brain dendritic spines and structure [10, 13, 37]. However, the autoantibody-mediated immune pathologic mechanisms in the brain are still poorly understood.

A final area of interest was exploration of the relationship between the ASD and non-ASD specific peptide sequences and the epitope repertoire reported in the Immune Epitope Database (IEDB) [38]. This interest stemmed from the potential of peptide mimicry identification to provide some understanding of how autoantibodies against these self-proteins are generated. We found that sequences DYPVVSIEDPFDQDD (SEQ ID NO:7), YPVVSIEDPFDQDDW (SEQ ID NO:8), PVVSIEDPFDQDDWA (SEQ ID NO:9), VVSIEDPFDQDDWAA (SEQ ID NO:10), and VSIEDPFDQDDWAAW (SEQ ID NO:11) are recognized by antibodies in both experimental groups indicating an immunodominant epitope recognized by the general population. As anticipated, these sequences share a high degree of homology with alpha and gamma enolase (NNE and NSE) at 90% stringency, and interestingly share 80% homology with other proteins including Protein ORF73 from human gamma-herpesvirus 8 (Mononucleosis causing agent), Protein X from Hepatitis B virus and Serpin H1 from humans indicating possible molecular mimicry to direct exposure to these agents.

B. Peptide Epitopes

In certain aspects, the present disclosure provides isolated peptides that specifically bind to maternal antibodies that are generated in the mother or potential mother against the neuron specific enolase (NSE) protein. NSE is a catalytic enzyme expressed on neurons and neuroendocrine tissues that mediates the conversion of 2-phospoglycerate (2PG) to 2-phophoenol pyruvate (2PEP) and the reverse reaction (2PEP to 2PG) in the glycolysis and gluconeogenesis pathways, respectively [16]. For eukaryotic cells, there are three enolase isoforms that are encoded by different genes and with tissue-specific expression; a enolase (ENO 1) is ubiquitously expressed, γ enolase (ENO 2) is found exclusively in neurons, and β enolase (ENO 3) is found only in muscle. The enolases are present as dimers and their function depends on the natural cofactor Mg+ to regulate the conformational and catalytic activity of the enzyme [17]. In the brain, NSE is expressed as γγ on neurons and αγ on microglia, astrocytes and oligodendrocytes. Non-neural enolase (NNE, αα dimer) is observed on neural tissue during the early phase of development, but changes to the γγ and αγ isoforms (NSE) as neural and glia differentiation and maturation take place, and it has been implicated in cell metabolism, modulation of the immune response, neuroinflammation, neurodevelopment, and brain homeostasis by regulating cell survival/death signals [18]. Thus, the potential for NSE as a target for maternal autoantibodies in the context of ASD is well-founded due to its clear role in neurodevelopmental biology.

In a first aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:1-6 (DVAASEFYRDGKYDL (SEQ ID NO:1); IEDPFDQDDWAAWSK (SEQ ID NO:2); ERLAKYNQLMRIEEE (SEQ ID NO:3); RLAKYNQLMRIEEEL (SEQ ID NO:4); DYPVVSIEDPFDQDDWAAW (SEQ ID NO:5); and SERLAKYNQLMRIEE (SEQ ID NO:6)). In some embodiments, the peptide comprises at least about 5, 6, 7, 8, 9, 10, 11, 12, 13, 14, or 15 contiguous amino acids of the amino acid sequence of any one of SEQ ID NOS:1-6. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:1-6. In some embodiments, the peptide comprises an amino acid sequence comprising or consisting of the amino acid sequence of any one of SEQ ID NOS:1-6. In other embodiments, the peptide comprises one or more additional amino acid residues at the amino-terminus and/or carboxyl-terminus that correspond to the amino acid residues at those positions in an NSE polypeptide sequence. In particular embodiments, the peptide binds to a maternal antibody that binds to an NSE polypeptide.

In some embodiments, the peptide is between about 5 to about 45 amino acids in length, between about 8 to about 45 amino acids in length, between about 8 to about 25 amino acids in length, between about 12 to about 45 amino acids in length, between about 5 to about 40 amino acids in length, between about 10 to about 40 amino acids in length, between about 15 to about 30 amino acids in length, between about 15 to about 25 amino acids in length, between about 15 to about 22 amino acids in length, between about 15 to about 20 amino acids in length, between about 17 to about 25 amino acids in length, between about 19 to about 25 amino acids in length, or about 45, 40, 35, 30, 25, 20, 15, 10, or 5 amino acids in length. For example, the peptide may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more amino acids in length. Typically, the peptide should not exceed a length which would allow the formation of a tertiary structure, such as, for example, greater than 45 amino acids if present as an isolated molecule. However, the peptide may exceed 45 amino acids if fused to a larger molecule such as an antibody or another protein or macromolecule which could prevent the formation of a tertiary structure within the peptide. The peptide may also exceed 45 amino acids if it is a bivalent peptide having first and second peptide fragments that bind to different maternal antibodies. In particular embodiments, the peptide is up to about 15, 20, 25, 30, 35, 40, or 45 amino acids in length.

In some embodiments, the peptide further comprises a label such as a detectable label. In certain instances, the label is selected from the group consisting of biotin, a fluorescent label, a chemiluminescent label, and a radioactive label. In certain other instances, the label is covalently attached to the peptide.

In other embodiments, the peptide includes variants that are further modified to improve their resistance to proteolytic degradation or to optimize solubility properties or to render them more suitable as a therapeutic agent. For example, the peptide further includes analogs containing residues other than naturally occurring L-amino acids, e.g., D-amino acids or non-naturally occurring synthetic amino acids. D-amino acids may be substituted for some or all of the amino acid residues.

In certain embodiments, the peptide comprises naturally-occurring amino acids and/or unnatural amino acids. Examples of unnatural amino acids include, but are not limited to, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of naturally-occurring amino acids (e.g., trifluorotyrosine, p-Cl-phenylalanine, p-Br-phenylalanine, p-I-phenylalanine, etc.), L-allyl-glycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine (e.g., 1-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid, L-Phe (4-benzyl), etc.). The peptide may be further modified. For example, one or more amide bonds may be replaced by ester or alkyl backbone bonds. There may be N- or C-alkyl substituents, side-chain modifications, or constraints such as disulfide bridges or side-chain amide or ester linkages.

In some embodiments, the peptide includes both modified peptides and synthetic peptide analogues. Peptides may be modified to improve formulation and storage properties, or to protect labile peptide bonds by incorporating non-peptidic structures.

In other embodiments, the peptide may be cyclized. Methods are well known in the art for introducing cyclic structures into peptides to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclization methods include the formation of thioethers and carboxyl- and amino-terminal amides and esters. A number of synthetic techniques have been developed to generate synthetic circular peptides (see, e.g., Tarn et al., *Protein Sci.,* 7:1583-1592 (1998); Romanovskis et al., *J. Pept. Res.,* 52: 356-374 (1998); Camarero et al., *J. Amer. Chem. Soc.,* 121: 5597-5598 (1999); Valero et al., *J. Pept. Res.,* 53(1): 56-67 (1999)). Generally, the role of cyclizing peptides is twofold: (1) to reduce hydrolysis in vivo; and (2) to thermodynamically destabilize the unfolded state and promote secondary structure formation.

In some embodiments, the present disclosure provides a plurality of peptides that includes at least two of the same peptide or different peptides linked covalently or non-covalently. For example, in some embodiments, at least two, three, four, five, or six of the same peptide or different peptides are linked covalently, e.g., so that they will have the appropriate size and/or binding properties, but avoiding unwanted aggregation.

The peptides described herein can be produced by any suitable means known or later discovered in the field, e.g., synthesized in vitro, purified or substantially purified from a natural source, recombinantly produced from eukaryotic or prokaryotic cells, etc.

The peptides may be prepared by in vitro synthesis, using conventional methods as known in the art. For example, peptides may be produced by chemical synthesis, e.g., using solid phase techniques and/or automated peptide synthesizers. In certain instances, peptides may be synthesized using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized. By using synthesizers, naturally-occurring amino acids may be substituted with unnatural amino acids. The particular sequence and the manner of preparation will be determined by convenience, economics, purity required, and the like. The peptides may alternatively be prepared by cleavage of a longer peptide or full-length protein sequence.

The peptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. Methods which are well known to those skilled in the art can be used to construct expression vectors containing coding sequences and appropriate transcriptional/translational control signals. These methods include, for example, in vitro recombinant DNA techniques, synthetic techniques, and in vivo recombination/genetic recombination. Alternatively, RNA capable of encoding the peptides of interest may be chemically synthesized. One of skill in the art can readily utilize well-known codon usage tables and synthetic methods to provide a suitable coding sequence for any of the peptides described herein. See, e.g., Sambrook and Russell, Molecular Cloning: A Laboratory Manual, 3rd Ed., 2001, Cold Spring Harbor Laboratory Press; and Ausubel, et al., Current Protocols in Molecular Biology, 1987-2009, John Wiley Interscience.

In other aspects, the present disclosure provides compositions comprising any one of the peptides described herein or a plurality thereof. As non-limiting examples, the compositions comprise a plurality of peptides that bind to maternal antibodies against NSE. As additional non-limiting examples, the compositions comprise one or more peptides selected from the group consisting of SEQ ID NOS:1-6. As further non-limiting examples, the compositions comprise peptides corresponding to SEQ ID NOS:1-6.

C. Mimotopes

In certain aspects, the present disclosure provides mimotopes which immunologically mimic a peptide epitope described herein (e.g., a peptide that binds to a maternal antibody that binds to the NSE protein). In some embodiments, the mimotope is a peptide sequence which immunologically mimics the peptide epitope and has sequence homology to the antigenic site. In other embodiments, the mimotope is a peptide sequence which immunologically mimics the peptide epitope and has a three-dimensional conformation, but not sequence homology, that is similar to the antigenic site.

In some embodiments, the mimotope causes an antibody response similar to the one elicited by the peptide epitope. In certain instances, the antibody response of the mimotope corresponds to binding to the same antigenic site on a maternal antibody to which a peptide epitope binds. The ability of the mimotope to act as a molecular mimic to bind to the maternal antibody can be used to block the antibody from binding to its original target antigen (e.g., NSE protein).

In some embodiments, the mimotope is obtained from phage display libraries through biopanning. Phage display libraries suitable for screening and identifying candidate mimotopes are typically a multiplicity of phages which express random amino acid sequences of less than 100 amino acids in length, less than 75 amino acids, less than 50 amino acids, less than 25 amino acids, and particularly within the range of about 3 to about 25 amino acids at a location which may be bound by an antibody.

In other embodiments, the mimotope is obtained by screening peptide libraries. In some instances, the peptide library is an overlapping peptide library. In other instances, the peptide library is a truncation peptide library, which may be used to identify the shortest amino acid sequence needed for activity. In yet other instances, the mimotope is obtained by alanine scanning, where alanine is used to substitute each residue sequentially to identify specific amino acid residues responsible for a peptide's activity. In further instances, the mimotope is obtained by positional scanning, which identifies an amino acid of interest at a single position and substitutes it with all other natural amino acids one at a time to identify preferred amino acid residues at that position for increasing a peptide's activity. In related instances, the positional scanning may comprise two position combinatorial scanning or three position combinatorial scanning. Additional methods for designing, screening, and determining mimotopes are described in, e.g., U.S. Pat. No. 4,833,092, the disclosure of which is incorporated by reference in its entirety for all purposes.

In further embodiments, the mimotope may comprise a peptide sequence which is structurally more constrained than a linear form of the sequence. An unsubstituted linear peptide such as present free in solution would normally be able to assume a large number of different conformations. In contrast, a peptide which is structurally constrained, perhaps by having one or usually two or more substituents which reduce in number the possible conformations which it can assume, is also within the scope of the present disclosure.

Substituents such as covalent linkages to further peptide chains or intramolecular linkages will structurally constrain the peptide. For example, the peptide may form part of the primary structure of a larger polypeptide containing the amino acid sequence of the peptide. In certain instances, the peptide comprises a cyclic peptide.

Other substituents include covalent linkages to other moieties such as macromolecular structures including biological and nonbiological structures. Examples of biological structures include, without limitation, carrier proteins. Examples of non-biological structures include lipid vesicles such as liposomes, micelles, lipid nanoparticles, and the like.

In some embodiments, the carrier protein is conjugated to the mimotope. A number of carriers are known for this purpose, including various protein-based carriers such as albumin (e.g., bovine serum albumin (BSA)), keyhole limpet hemocyanin (KLH), ovalbumin (OVA), tetanus toxoid (TT), high-molecular weight proteins (HMP) from nontypeable *Haemophilus influenzae*, diphtheria toxoid, or bacterial outer membrane protein, all of which may be obtained from biochemical or pharmaceutical supply companies or prepared by standard methodology).

In other embodiments, the mimotope is a component of a vaccine. The vaccine may incorporate one or a plurality of mimotopes in which each mimotope is capable of binding to the same or different maternal antibody to block the antibody from binding to its original target antigen (e.g., NSE protein). The plurality of mimotopes may be conjugated together, for example, using a polylysine to which each mimotope is conjugated.

In particular embodiments, peptide mimotopes are designed using single amino acid substitutions followed by affinity testing for each peptide construct to determine which peptide mimics have the ability to block autism-specific maternal autoantibodies. In certain instances, D-amino acids are used when synthesizing the peptide mimotopes as peptides synthesized from D-amino acids are more resistant to proteolytic digestion and have a longer half-life hi vivo. In other instances, peptide mimotopes for each autoantigen are fused to a polyethylene glycol (PEG) scaffold, which leads to the creation of a heteromultimer capable of neutralizing autism-specific maternal autoantibodies. See, e.g., Kessel et al., Chem Med Chem. 4(8):1364-70, 2009.

As peptides on a PEG scaffold are less immunogenic than individual peptides, the mimotope peptides linked to a PEG scaffold are useful as an antibody blocker. The peptide mimotopes may be synthesized with 9-fluorenyl-methoxycarbonyl-protected amino acid chemistry on appropriate polyethylene glycol (PEG)-PS resin (GenScript Corporation; Piscataway, NJ) by using an automated peptide synthesizer (Pioneer; Applied Biosystems; Foster City, CA). Cleavage of the peptides from the resin and removal of the protecting groups from the side chain may be carried out by using trifluoroacetic acid with scavengers. The crude peptides may be purified by reverse-phase high-performance liquid chromatography using a preparatory $C_{18}$ column with a gradient of solvent A [95%/5%, $H_2O$ (0.1% trifluoroacetic acid)/acetonitrile] and solvent B (100% acetonitrile). The purity of the peptides is then analyzed by high-performance liquid chromatography using an analytical Cis column. The identity of the synthesized peptide may also be confirmed by matrix-assisted laser desorption ionization/time of flight mass spectrometry. In certain instances, peptide mimotopes may be PEGylated using a strategy that involves the reversible protection of specific residues on the peptides. This procedure is possible for peptides only because they generally contain just a few nucleophilic groups and are more stable than full-length proteins toward the harsh chemical treatments involved in this process. This method involves three steps: (1) protection by suitable reagents of the residues known to be important for the activity and, eventually, the purification of the desired isomers; (2) PEGylation at the level of the lone unprotected, reactive target residue; and (3) removal of all the protecting groups.

To determine if the multimerized peptide mimotopes bind to anti-brain autoantibodies in patient serum, an ELISA assay may be utilized. ELISA assays may also be used to determine if the multimerized peptide mimotopes inhibit the antigen-antibody interaction against the native antigen protein. This may be accomplished by pre-incubating maternal antibody positive plasma with the heteromultimer before performing the ELISA.

An animal model may be used to examine the efficacy, safety, and/or pharmacokinetic properties of the peptide mimotopes in vivo. As a non-limiting example, a mouse model of maternal autoantibody related (MAR) autism may be used. See, e.g., Example 5 of International Patent Publication No. WO 2016/210137. MAR autism and control dams (i.e., pregnant female mice) may be randomly assigned to one of two treatment conditions: gestational mimotope treatment or a saline control. Once tolerance has been broken in MAR autism dams, dams assigned to the treatment group may be administered the mimotope peptides via intravenous injection. The efficacy of the mimotopes in vivo may be determined by administration of 200 μg of mimotope to the dam every 24 hours for a total of 4 injections. Reduction of murine autoantibody titer by the peptide mimotope following treatment may be determined using an ELISA assay against the whole target antigen protein. A series of treatment trials may be conducted to determine how many treatments are necessary to reduce/block the murine maternal antibodies for the duration of gestation. Upon determining the ideal treatment regime, dams may be bred to produce offspring for subsequent behavioral analyses.

In particular embodiments, the peptide is a mimotope comprising D-amino acids at some (e.g., at least 1, 2, 3, 4, 5, 6, 7, 8, 9, or 10) or all of the positions in the amino acid sequence and/or comprising amino acid modifications (e.g., substitutions) at one or more (e.g., at least 1, 2, 3, 4, 5, 6, 7, 8, 9, or 10) positions in the amino acid sequence relative to the amino acid sequence of any one of SEQ ID NOS:1-6.

D. Kits

The present disclosure also provides kits for the diagnosis or prognosis of whether an offspring such as a fetus or child is at an increased risk of developing an autism spectrum disorder (ASD). Relatedly, the kits also find use for the diagnosis or prognosis of whether a mother or potential mother is at an increased risk of bearing a child who will develop an ASD.

Materials and reagents to carry out these various methods can be provided in kits to facilitate execution of the methods. As used herein, the term "kit" includes a combination of articles that facilitates a process, assay, analysis, or manipulation. In particular, kits comprising the peptides or compositions described herein find utility in a wide range of applications including, for example, diagnostics, prognostics, immunotherapy, and the like.

In particular embodiments, the kits comprise any one or a plurality of the peptides described herein (e.g., peptide epitopes and mimotopes thereof) that specifically bind to maternal antibodies against the NSE antigen and a solid support. In some instances, the kits comprise peptides (e.g., peptide epitopes and/or mimotopes thereof) corresponding to any one of SEQ ID NOS:1-6 or combinations thereof.

In some embodiments, the solid support comprises at least one peptide, e.g., at least 1, 2, 3, 4, 5, or 6 peptides. In certain instances, the solid support comprises an NSE peptide epitope. In some embodiments, the solid support comprises one or more peptides having at least about 80%, 85%, 90%, 91%, 92%, 93%, 94%, 95%, 96%, 97%, 98%, 99%/o or 100%/o identity with the peptides described herein, e.g., with the amino acid sequence of any one of SEQ ID NOS:1-6. In other embodiments, the solid support comprises one or more peptides having the amino acid sequence set forth in any one of SEQ ID NOS:1-6 or fragments thereof.

In some embodiments, the peptide or plurality of peptides can be immobilized on the solid support. In other embodiments, the solid support is a multiwell plate, an ELISA plate, a microarray, a chip, a bead, a porous strip, or a nitrocellulose filter. The immobilization can be via covalent or non-covalent binding. In some embodiments, the immobilization is through a capture antibody that specifically binds to the one or more peptides. In certain instances, the solid support in the kits are provided prepared with one or more immobilized peptides.

In certain embodiments, the plurality of peptides in the kit comprises at least 2, 3, 4, 5, or 6 different peptides, e.g., selected from SEQ ID NOS:1-6 and mimotopes thereof. In certain instances, each of the different peptides in the kit binds to the same maternal antibodies, e.g., all of the different peptides bind to maternal antibodies against the NSE antigen.

In particular embodiments, the plurality of peptides in the kit make up one or more panels, wherein each panel contains a combination of peptides that bind to maternal antibodies against the NSE antigen. As non-limiting examples, each panel contains a combination of peptides that bind to maternal antibodies against the NSE antigen. As additional non-limiting examples, the kits contain one or more combinations of peptides selected from the group consisting of SEQ ID NOS:1-6, in which each combination has 2, 3, 4, 5, or 6 peptides selected from the peptides of SEQ ID NOS:1-6.

Kits can contain chemical reagents as well as other components. In addition, the kits described herein can include, without limitation, instructions to the kit user, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits described herein can also be packaged for convenient storage and safe shipping, for example, in a box having a lid.

In some embodiments, the kits also comprise labeled secondary antibodies used to detect the presence of maternal autoantibodies that bind to one or more peptides. The secondary antibodies bind to the constant or "C" regions of different classes or isotypes of immunoglobulins IgM, IgD, IgG, IgA, and IgE. Usually, a secondary antibody against an IgG constant region is included in the kits, such as, e.g., secondary antibodies against one of the IgG subclasses (e.g., IgG1, IgG2, IgG3, and IgG4). Secondary antibodies can be labeled with any directly or indirectly detectable moiety, including a fluorophore (e.g., fluoroscein, phycoerythrin, quantum dot, Luminex bead, fluorescent bead), an enzyme (e.g., peroxidase, alkaline phosphatase), a radioisotope (e.g., $^{3}H$, $^{32}P$, $^{125}I$), or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, OR. Enzyme-labeled anti-human IgG antibodies are commercially available from Sigma-Aldrich, St. Louis, MO and Chemicon, Temecula, CA.

The kits may further comprise instructions for contacting the solid support with a biological sample from a mother or potential mother, and for correlating the presence of maternal antibodies or levels of maternal antibodies above a threshold level with an increased probability that a fetus or child of the mother or potential mother will develop an ASD.

In some embodiments, the kits also contain negative and positive control samples for detection of maternal antibodies. In some instances, the negative control samples are obtained from mothers who have TD children. In other instances, the negative and/or positive control samples are reactive to the NSE antigen. In yet other instances, the negative and/or positive control samples do not react to the NSE antigen. In some embodiments, the kits contain samples for the preparation of a titrated curve of maternal antibodies in a sample, to assist in the evaluation of quantified levels of antibodies in a test biological sample. In particular embodiments, the kit comprises one or more peptides described in SEQ ID NOS:1-6, e.g., 1, 2, 3, 4, 5, or 6 of the peptides described in SEQ ID NOS:1-6.

The kits find use for providing a diagnosis or prognosis to any women of childbearing age. A diagnosis or prognosis can be determined before, during, or after pregnancy. Detection of maternal antibodies can be made in one or more of the first, second, and/or third trimesters of pregnancy. In some embodiments, detection of maternal antibodies is performed on a biological sample from a woman carrying a fetus whose brain has begun to develop, e.g., after about 12 weeks of gestation. In some embodiments, the presence or absence of maternal antibodies or the quantified levels of maternal antibodies are evaluated one or more times postpartum, e.g., in the first four weeks after birth and/or while the mother is breastfeeding the child. In some embodiments, the presence of maternal antibodies or the quantified levels of maternal antibodies are evaluated one or more times before pregnancy or in any woman who is not pregnant.

E. Patients Subject to Diagnosis or Treatment

The methods described herein can be performed on any mammal, for example, a human, a non-human primate, a laboratory mammal (e.g., a mouse, a rat, a rabbit, a hamster), a domestic mammal (e.g., a cat, a dog), or an agricultural mammal (e.g., bovine, ovine, porcine, equine). In some embodiments, the patient is a woman and a human.

Any woman capable of bearing a child can benefit from the methods described herein. The child may or may not be conceived, i.e., the woman can be but need not be pregnant. In some embodiments, the woman has a child who is a neonate. In some embodiments, the woman is of childbearing age, i.e., she has begun to menstruate and has not reached menopause.

In some embodiments, the diagnostic and prevention and/or treatment methods described herein are performed on a woman carrying a fetus (i.e., who is pregnant). The methods can be performed at any time during pregnancy. In some embodiments, the methods are performed on a woman carrying a fetus whose brain has begun to develop. For example, the fetus may at be at about 12 weeks of gestation or later. In some embodiments, the woman subject to treatment or diagnosis is in the second or third trimester of pregnancy. In some embodiments, the woman subject to treatment or diagnosis is in the first trimester of pregnancy. In some embodiments, the woman is post-partum, e.g., within 6 month of giving birth. In some embodiments, the woman is post-partum and breastfeeding.

Women who will benefit from the present methods may but need not have a familial history of an ASD or an autoimmune disease. For example, the woman may have an ASD or have a family member (e.g., a parent, a child, a grandparent) with an ASD. In some embodiments, the woman suffers from an autoimmune disease or has a family member (e.g., a parent, a child, a grandparent) who suffers from an autoimmune disease.

In some embodiments, the methods described herein comprise the step of determining that the diagnosis or treatment is appropriate for the patient, e.g., based on prior medical history or familial medical history or pregnancy status or any other relevant criteria.

F. Methods of Determining Risk of Developing Autism Spectrum Disorder

In certain aspects, the present disclosure provides methods for determining the likelihood or risk that a fetus or child will develop an autism spectrum disorder (ASD) comprising identifying in a biological sample from the mother or potential mother of the fetus or child the presence of maternal autoantibodies that bind to the NSE antigen. The methods comprise detecting in the biological sample the presence or absence of maternal autoantibodies that bind to any one of the peptides described herein or a plurality thereof, wherein the presence of maternal autoantibodies that bind to the peptide or plurality thereof indicates an increased likelihood or risk that the fetus or child will develop an ASD.

With respect to the biological sample taken from the mother or potential mother, any fluid sample containing antibodies can be used. For example, the biological sample may be blood, serum, plasma, amniotic fluid, urine, breast milk or saliva. Of course, one or more different bodily fluids can be evaluated for antibodies that specifically bind to the one or more peptides.

In particular embodiments, the biological sample is evaluated for the presence of maternal antibodies that specifically bind to at least one or more of the peptides described herein (e.g., SEQ ID NOS:1-6), e.g., at least 1, 2, 3, 4, 5, or 6 of the peptides set forth in SEQ ID NOS:1-6. In some embodiments, the presence of maternal antibodies that specifically bind the NSE antigen is detected in the sample using one or more of the peptides described herein (e.g., SEQ ID NOS: 1-6). As a non-limiting example, one or more peptides, e.g., 1, 2, 3, 4, 5, or 6 different peptides as set forth in SEQ ID NOS:1-6, can be used to detect the presence or absence of maternal antibodies in the sample.

In certain instances, the presence of maternal antibodies against NSE can be detected using 1, 2, 3, 4, 5, or 6 peptides set forth in SEQ ID NOS:1-6 or antigenic fragments thereof.

In some embodiments, detection of the presence of maternal antibodies (versus the absence of detection of maternal antibodies) indicates an increased probability that the fetus or child has or will develop an ASD.

In some embodiments, the level or titer of the maternal antibodies in the biological sample is compared to a threshold level or titer. A level or titer of the antibodies in the biological sample that is greater than the threshold level or titer indicates an increased probability that the fetus or child has or will develop an ASD. Likewise, a level or titer of the antibodies in the biological sample that is less than the threshold level or titer does not indicate an increased probability (i.e., indicates no increased probability) that the fetus or child has or will develop an ASD. The threshold level or titer for maternal antibodies in a particular biological fluid can be determined by evaluating levels of maternal antibodies in populations of pregnant women and comparing the antibody levels or titer in the biological fluid of the mother when the child developed an ASD and to the antibody levels or titer in the biological fluid of the mother when the child did not develop an ASD. The threshold levels or titer can also be determined at different time points during pregnancy, e.g., every four weeks, every two weeks or every week during gestation of the fetus. Threshold antibody levels or titer can also be measured after the child is born, e.g., in the first four weeks after birth and/or while the mother is breastfeeding the child.

The presence of the maternal antibodies against the NSE antigen or the quantified levels of the maternal antibodies against the NSE antigen can be determined before, during, or after pregnancy. When determined during pregnancy, detection of the maternal antibodies can be performed one, two, three, four or more times, as appropriate, at any time during the course of pregnancy. For example, detection of the maternal antibodies can be made in one or more of the first, second and/or third trimesters of pregnancy. In some embodiments, detection of the maternal antibodies is performed on a biological sample from a woman carrying a fetus whose brain has begun to develop, e.g., after about 12 weeks of gestation. In some embodiments, the presence or absence of maternal antibodies or the quantified levels of maternal antibodies are evaluated one or more times post-partum, e.g., in the first four weeks after birth and/or while the mother is breastfeeding the child. In some embodiments, the presence or absence of the maternal antibodies or the quantified levels of the maternal antibodies are evaluated one or more times before pregnancy or in any women who is not pregnant.

The presence of the maternal antibodies may be determined once or more than once, as needed or desired. In some embodiments, the presence or absence of maternal antibodies or the quantified levels of maternal antibodies are evaluated every four weeks, every two weeks or every week during pregnancy, or more or less often, as appropriate.

In some embodiments, presence of the maternal antibodies is made without comparing the test sample (i.e., a biological sample from the mother or potential mother) to a control sample. In other embodiments, the test sample is compared to a control. The control can be from the same individual at a different time point. For example, the test sample can be taken during pregnancy, and the control sample can be taken from the same individual before pregnancy. In some instances, the test sample will be taken relatively later in pregnancy term and the control sample will be taken from the same individual earlier in pregnancy term. In this case, if the level of maternal antibodies is greater in the test sample than in the control sample, then the fetus or child is at an increased risk of developing an ASD. If several samples are evaluated over the course of a pregnancy, increased levels or titers of maternal antibodies over the term of the pregnancy indicate an increased risk that the fetus or child will develop an ASD. Similarly, absent or decreased levels or titers of the maternal antibodies over the term of the pregnancy indicate a low or reduced risk that the fetus or child will develop an ASD.

The control can also be from a different individual with a known status for the presence of the maternal antibodies. The control can also be a calculated value from a population of individuals with a known status for the presence of maternal antibodies. The control may be a positive control or a negative control. In some instances, the negative control is obtained from a mother who has a TD child. In other instances, the negative and/or positive control sample reacts to the NSE antigen. In yet other instances, the negative and/or positive control sample does not react to the NSE antigen.

In some embodiments, the control is a negative control from another individual or a population of individuals. If the known status of the control sample is negative for the antibodies, then a higher level of maternal antibodies in the test sample than in the negative control sample indicates that the fetus or child is at an increased risk of developing an ASD. A similar level of maternal antibodies in the test sample to the negative control sample indicates that the fetus or child is not at an increased risk, i.e., has a low or reduced risk, of developing an ASD.

In some embodiments, the control is a positive control from another individual or a population of individuals, or the control reflects a predetermined threshold level of antibodies. If the known status of the control sample is positive for antibodies, then a similar or higher level of maternal antibodies in the test sample than in the positive control sample indicates that the fetus or child is at an increased risk of developing an ASD. A lower level of maternal antibodies in the test sample to the control sample indicates that the fetus or child is not at an increased risk or has a low or reduced risk of developing an ASD.

The differences between the control sample or value and the test sample need only be sufficient to be detected. In some embodiments, an increased level of maternal antibodies in the test sample, and hence an increased risk of an ASD, is determined when the antibody levels are at least, e.g., 10%, 25%, 50%, 1-fold, 2-fold, 3-fold, 4-fold, or more in comparison to a negative or a prior-measured control.

For the purposes of diagnosing an increased likelihood that a fetus or child will develop an ASD, the presence of maternal antibodies against any subtype, isoform or isozyme of the NSE antigen can be determined.

The maternal antibodies can be detected using any method known in the art. Exemplary methods include, without limitation, Western Blot, dot Blot, enzyme-linked immunosorbent assay (ELISA), radioimmunoassay (RIA), electrochemiluminescence, and multiplex bead assays (e.g., using Luminex or fluorescent microbeads).

The peptides can be antigenic fragments of the NSE antigen. The peptides can be derived from known antigenic epitopes of the NSE antigen, with one or more amino acids substituted, deleted, added, or otherwise modified. The peptides can be purified or substantially purified from a natural source, or recombinantly or synthetically produced.

In some embodiments, the peptides used to detect maternal antibodies can be immobilized on a solid support. The solid support can be, for example, a multiwell plate, a microarray, a chip, a bead, a porous strip, or a nitrocellulose filter. The immobilization can be via covalent or non-covalent binding. In some embodiments, the immobilization is through a capture antibody that specifically binds to the target epitope.

For detection of maternal antibodies, a sample can be incubated with one or more of the peptides described herein under conditions (e.g., time, temperature, concentration of sample) sufficient to allow specific binding of any antibodies that specifically bind to one or more target antigens present in the sample. The one or more peptides can be bound to a solid support. For example, the one or more peptides can be exposed to a sample for about 0.5, 1.0, 1.5, 2.0, 2.5, 3.0 hours, or overnight, about 8, 10, 12, 14, or 16 hours. However, incubation time can be more or less depending on, e.g., the composition of the one or more peptides, the composition of the one or more target antigens, the dilution of the sample, and the temperature for incubation. Incubations using less diluted samples and higher temperatures can be carried out for shorter periods of time. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

Labeled secondary antibodies are generally used to detect antibodies in a sample that have bound to one or more of the peptides described herein. Secondary antibodies bind to the constant or "C" regions of different classes or isotypes of immunoglobulins IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluoroscein, phycoerythrin, quantum dot, Luminex bead, fluorescent bead), an enzyme (e.g., peroxidase, alkaline phosphatase), a radioisotope (e.g., $^{3}H$, $^{32}P$, $^{125}I$) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, OR. Enzyme-labeled anti-human IgG antibodies are commercially available from Sigma-Aldrich, St. Louis, MO and Chemicon, Temecula, CA.

The method of detection of the presence or absence, or differential presence, of autoantibodies in a sample will correspond with the choice of label of the secondary antibody. For example, if one or more of the peptides described herein are transferred onto a membrane substrate suitable for immunoblotting, the detectable signals (i.e., blots) can be quantified using a digital imager if enzymatic labeling is used or an x-ray film developer if radioisotope labeling is used. In another example, if one or more of the peptides described herein are transferred to a multi-well plate, the detectable signals can be quantified using an automated plate reader capable of detecting and quantifying fluorescent, chemiluminescent, and/or colorimetric signals. Such methods of detection are well known in the art.

General immunoassay techniques are well known in the art. Guidance for optimization of parameters can be found in, for example, Wu, Quantitative Immunoassay: A Practical Guide for Assay Establishment, Troubleshooting, and Clinical Application, 2000, AACC Press; Principles and Practice of Immunoassay, Price and Newman, eds., 1997, Groves Dictionaries, Inc.; The Immunoassay Handbook, Wild, ed., 2005, Elsevier Science Ltd.; Ghindilis, Pavlov and Atanassov, Immunoassay Methods and Protocols, 2003, Humana Press; Harlow and Lane, Using Antibodies. A Laboratory Manual, 1998, Cold Spring Harbor Laboratory Press; and Immunoassay Automation: An Updated Guide to Systems, Chan, ed., 1996, Academic Press.

In certain embodiments, the presence or increased presence of maternal antibodies is indicated by a detectable signal (e.g., a blot, fluorescence, chemiluminescence, color, radioactivity) in an immunoassay, where the biological sample from the mother or potential mother is contacted with one or more of the peptides described herein. This detectable signal can be compared to the signal from a control sample or to a threshold value. In some embodiments, increased presence is detected, and an increased risk of ASD is indicated, when the detectable signal of maternal antibodies in the test sample is at least about 10%, 20%, 30%, 50%, 75% greater in comparison to the signal of maternal antibodies in the control sample or the predetermined threshold value. In some embodiments, an increased presence is detected, and an increased risk of ASD is indicated, when the detectable signal of maternal antibodies in the test sample is at least about 1-fold, 2-fold, 3-fold, 4-fold or more, greater in comparison to the signal of maternal antibodies in the control sample or the predetermined threshold value.

In some embodiments, the results of the maternal antibody determinations are recorded in a tangible medium. For example, the results of the present diagnostic assays (e.g., the observation of the presence or increased presence of maternal antibodies) and the diagnosis of whether or not an increased risk of ASD is determined can be recorded, e.g., on paper or on electronic media (e.g., audio tape, a computer disk, a CD, a flash drive, etc.).

In other embodiments, the methods further comprise the step of providing the diagnosis to the patient (i.e., the mother or potential mother) of whether or not there is an increased risk that a fetus or child of the patient will develop an ASD based on the results of the maternal antibody determinations.

G. Methods of Reducing Risk by Administering Peptide Epitopes

In certain aspects, the present disclosure provides methods for preventing and/or reducing the risk of developing an autism spectrum disorder (ASD) in a fetus or child by administering in vivo to the mother or potential mother a blocking agent, e.g., an NSE peptide described herein or a mimotope thereof that specifically binds to maternal autoantibodies associated with ASD. The blocking agent can prevent the maternal antibodies from specifically binding the endogenous NSE autoantigen present in the fetus or child.

In some embodiments, the methods include administering to the mother or potential mother at least one blocking agent comprising at least one or more of the peptides described herein (e.g., SEQ ID NOS:1-6) or mimotopes thereof, e.g., at least 1, 2, 3, 4, 5, or 6 of the peptides set forth in SEQ ID NOS:1-6 or mimotopes thereof. In certain instances, the blocking agent comprises peptides or mimotopes thereof corresponding to SEQ ID NOS:1-6, and combinations thereof. In some instances, the blocking agent specifically binds to a maternal antibody that recognizes the NSE antigen.

The prevention and/or treatment methods of the present disclosure using a blocking agent or plurality of blocking agents can be provided to a woman before, during, or after pregnancy. In some embodiments, the blocking agent(s) can be administered one, two, three, four or more times, as appropriate, at any time during the course of pregnancy. For example, the blocking agent(s) can be administered in one or more of the first, second and/or third trimesters of pregnancy. In some embodiments, the blocking agent(s) are administered to a woman carrying a fetus whose brain has begun to develop, e.g., after about 12 weeks of gestation. In some embodiments, the blocking agent(s) are administered one or more times post-partum, e.g., in the first four weeks after birth and/or while the mother is breastfeeding the child. In some embodiments, the blocking agent(s) are administered one or more times before pregnancy, for example, in a woman who has tested positive for maternal antibodies and who is trying to become pregnant.

In some embodiments, a plurality of agents comprising two or more peptides or mimotopes thereof are administered. The plurality of agents can be administered separately or together. The plurality of agents can be a pool of individual peptides or mimotopes. In some embodiments, two or more peptides or mimotopes having different epitopes are chemically linked. The multiple antigenic epitopes can be from the same or different antigenic polypeptides. Chemical linkage in this case may be by direct linking of the peptides or linkage through the use of a chemical scaffold or linker. In some embodiments, two or more peptides or mimotopes having different peptide epitopes are fused together. The peptide epitope fusions can be expressed recombinantly or chemically synthesized.

In some embodiments, the methods further comprise the step of administering to the mother or potential mother a therapeutic or preventative regime of one or more blocking agents (e.g., one or more of the peptides of SEQ ID NOS:1-6 or mimotopes thereof) to reduce, inhibit, or prevent the binding of maternal autoantibodies to the NSE antigen.

In certain instances, the administered blocking agent or plurality of blocking agents that reduce, inhibit, or prevent the binding of maternal antibodies to an NSE polypeptide comprises 1, 2, 3, 4, 5, or 6 of the peptides set forth in SEQ ID NOS:1-6 or antigenic fragments or mimotopes thereof. In other instances, the administered blocking agent or plurality of blocking agents that reduce, inhibit, or prevent the binding of maternal antibodies to an NSE polypeptide comprises 1, 2, 3, 4, 5, or 6 of the peptides as set forth in SEQ ID NOS:1-6 or antigenic fragments or mimotopes thereof.

The administered blocking agents may contain modifications to reduce or minimize their immunogenicity. Modifications to amino acids in the peptides or mimotopes include, but are not limited to, an amide moiety or a pyroglutamyl residue or the addition of polyethylene glycol chains (PEGylation). These modifications may contribute to decreasing the propensity to form R-sheet conformation or may contribute to peptide stability, solubility and decreased immunogenicity. In some instances, a more stable, soluble and less immunogenic peptide is desirable. Many peptides modified at the C-terminus with a $CONH_2$ (amide) group appear to be resistant to attack by carboxypeptidases and many peptides having a pyroglutamyl residue at the N-terminus are more resistant to attack by broad specificity aminopeptidases. PEGylated peptides have been shown to have increased plasma half-lives and decreased immunogenicity as compared with non-modified peptides. Furthermore, sequence analysis of the blocking agents will allow the minimization of known T-cell epitopes through conservative modifications. Also included as peptides described herein are cyclic peptides that are resistant to attack by both carboxypeptidases and aminopeptidases. Additionally, oral administration of the blocking agent may aid in minimizing immunogenicity.

In some embodiments, the prevention and/or treatment methods include the step of first determining the presence or increased presence of maternal antibodies that bind to the NSE antigen in the mother or potential mother using the detection methods described herein. A woman who tests positive or at a level above the threshold level for the presence of maternal antibodies is a candidate to receive a blocking agent(s) that specifically binds to the maternal antibodies. A woman who tests negative or at a level below the threshold level for the presence of maternal antibodies need not receive a blocking agent(s) that specifically binds to the maternal antibodies.

Pharmaceutical compositions suitable for use in the present disclosure include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein. Generally, an efficacious or effective amount of one or more maternal antibody blocking agents is determined by first administering a low dose or small amount of a blocking agent and then incrementally increasing the administered dose or dosages, and/or adding a second blocking agent(s) as needed, until a desired effect of, e.g., eliminating or reducing the presence of unbound or free maternal antibodies below a predetermined threshold level, is observed in the treated subject, with minimal or no toxic or undesirable side-effects. Applicable methods for determining an appropriate dose and dosing schedule for administration of a pharmaceutical composition of the present disclosure is described, for example, in Goodman and Gilman's The Pharmacological Basis of Therapeutics, 11th Ed., Brunton, et al., Eds., McGraw-Hill (2006), and in Remington: The Science and Practice of Pharmacy, 21st Ed., University of the Sciences in Philadelphia (USIP), 2005, Lippincott, Williams and Wilkins.

Dosage amount and interval can be adjusted individually to provide plasma or tissue levels of the blocking agent(s) sufficient to maintain a therapeutic effect. Single or multiple administrations of the compositions comprising an effective amount of one or more blocking agents can be carried out with dose levels and pattern selected by the treating physician. The dose and administration schedule can be determined and adjusted, e.g., based on the levels of maternal antibodies in the mother or potential mother, which can be monitored throughout the course of treatment according to methods commonly practiced by clinicians or those described herein. In some embodiments, therapeutic levels will be achieved by administering single daily doses. In other embodiments, the dosing schedule can include multiple daily dose schedules. In still other embodiments, dosing every other day, semi-weekly, or weekly are included in the present disclosure.

For example, the blocking agent(s) can be administered monthly, bi-weekly, weekly or daily, as needed. In some embodiments, the levels of maternal antibodies in the mother or potential mother are monitored and the blocking agent(s) are administered if maternal antibodies are present or are present at levels above a predetermined threshold level. The blocking agent(s) can be administered for a time period of about 1, 2, 3, 4, 5, 10, 12, 15, 20, 24, 30, 32, 36 weeks, or longer or shorter, as appropriate. For example, administration of the blocking agent(s) can be discontinued if the level of maternal antibodies falls below the predetermined threshold level. The blocking agent(s) can be administered for the full duration of a pregnancy, or during one or more of the first, second or third trimesters of pregnancy. Administration can begin before conception and can continue after birth, for example, while the mother is breastfeeding the child.

In some embodiments where the blocking agent(s) is a peptide or mimotope thereof, typical dosages can range from about 0.1 μg/kg body weight up to and including about 1 g/kg body weight, for example, between about 1 μg/kg body weight to about 500 mg/kg body weight. In some embodiments, the dose of peptide or mimotope is about 1, 2, 3, 4, 5, 10, 20, 30, 40, 50, 60, 70, 80, 90, or 100 mg/kg body weight.

The exact dose will depend on a variety of factors as described herein, including the particular inhibitor, severity of the disease, and route of administration. Determining the exact therapeutically effective dose can be determined by a clinician without undue experimentation and can include any dose included within the ranges disclosed above.

The blocking agent(s) are administered by a route of administration such that the agent(s) bind to the maternal antibodies and prevents the binding of the antibodies to endogenous autoantigens associated with risk of developing ASD and that immune responses to the agent are minimized. Usually the agent(s) are administered systemically. In some embodiments, the agent(s) are administered parenterally, e.g., intravenously or intra-amniotically (i.e., directly into the amniotic sac). Additionally, the agent(s) may be administered orally.

The blocking agent(s) can be formulated for parenteral administration by injection, e.g., by bolus injection or continuous infusion. For injection, blocking agent(s) can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, a combination of blocking agents can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the blocking agent(s) in water-soluble form. Additionally, suspensions of the blocking agent(s) can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the blocking agent(s) can be in powder form for constitution with a suitable vehicle, e.g., sterile pyrogen-free water, before use.

Treatment with the blocking agent(s) is considered efficacious if the levels or titer of maternal antibodies that actively bind to the NSE antigen are reduced or eliminated in a biological sample from an individual after receiving one or more administrations of the blocking agent(s), in comparison to before administration of the blocking agent(s). For example, a reduction of maternal antibodies that actively bind to the NSE antigen in a sample of at least about 10%, 25%, 50%, 75% or 100% after one or more administrations of one or more blocking agents indicates that administration of the blocking agent(s) was efficacious. Where a threshold level has been established, treatment with the blocking agent(s) is considered efficacious if the levels or titer of maternal antibodies that actively bind to the NSE antigen are reduced to below the threshold level. Maternal antibodies that actively bind to the NSE antigen can be measured using any method known in the art, including those described herein.

H. Methods of Reducing Risk by Removing Maternal Antibodies

In certain aspects, the present disclosure provides methods of preventing or reducing a risk of an offspring such as a fetus or child for developing an autism spectrum disorder (ASD) by removing the maternal antibodies from a biological fluid of the mother or potential mother ex vivo, and then returning the biological fluid, with reduced or eliminated levels of maternal antibodies, to the mother or potential mother.

In some embodiments, biological fluid containing maternal antibodies can be removed from the mother or potential mother and contacted with one or more of the peptides described herein. In other embodiments, one or more of the peptides described herein can be administered to the mother or potential mother to block the binding between maternal autoantibodies and their autoantigens in a biological fluid, thereby neutralizing the maternal autoantibodies, and the neutralized complexes present in the biological fluid are removed using an extracorporeal therapy, such as affinity plasmapheresis.

In some embodiments, biological fluid from the mother or potential mother is contacted with one or more of the peptides immobilized on a solid support. The solid support can be, for example, a multiwell plate, an ELISA plate, a microarray, a chip, a bead, a column, a porous strip, a membrane, or a nitrocellulose filter. The immobilization can be via covalent or non-covalent binding. In some embodiments, the immobilization is through a capture antibody that specifically binds to the target peptide epitope. The peptide(s) attached to the solid support is a stationary phase that captures the maternal antibodies in the biological fluid, allowing the biological fluid with reduced or eliminated levels of maternal antibodies to be separated from the solid support, i.e., as the mobile phase, and returned to the mother or potential mother.

In some embodiments, the biological fluid that is processed ex vivo is plasma, and the maternal antibodies are removed by plasmapheresis, a process well known in the art. The plasma is contacted with a solid support with one or more immobilized peptides. Maternal antibodies in the plasma bind to the immobilized peptides. Plasma with reduced or eliminated levels of maternal antibodies is then returned to the mother or potential mother.

The ex vivo removal of maternal antibodies can be carried out on a woman before, during, or after pregnancy. In some embodiments, the maternal antibodies are removed from the biological fluid one, two, three, four or more times, as appropriate, at any time during the course of pregnancy. For example, the maternal antibodies can be removed in one or more of the first, second and/or third trimesters of pregnancy. In some embodiments, the maternal antibodies are removed from a woman carrying a fetus whose brain has begun to develop, e.g., after about 12 weeks of gestation. In some embodiments, the maternal antibodies are removed one or more times post-partum, e.g., in the first four weeks after birth and/or while the mother is breastfeeding the child. In some embodiments, the maternal antibodies are removed one or more times before pregnancy, for example, in a woman who has tested positive for maternal antibodies and who is trying to become pregnant.

The process of ex vivo maternal antibody removal can be performed one, two, three, four, or more times, as needed to eliminate or reduce maternal antibodies from the mother or potential mother. Ex vivo removal of the maternal antibodies can be performed daily, weekly, bi-weekly, monthly, bi-monthly, as appropriate. In some embodiments, the levels of maternal antibodies in the mother or potential mother are monitored and ex vivo maternal antibody removal performed if the presence of maternal antibodies are above a predetermined threshold level. Ex vivo maternal antibody removal can be carried out over a time period of a 1, 2, 3, 4, 5, 10, 12, 15, 20, 25, 35, 36 weeks, or longer or shorter, as appropriate. For example, ex vivo removal of maternal antibodies can be discontinued if the level of maternal antibodies falls below the predetermined threshold level. & vivo maternal antibody removal can be conducted for the full duration of a pregnancy, or during one or more of the first, second or third trimesters of pregnancy. Maternal antibody removal can begin before conception and can continue after birth, for example, while the mother is breastfeeding the child.

The biological fluid containing maternal antibodies is usually blood, serum, plasma, or milk. In some embodiments, the biological fluid is amniotic fluid.

EXAMPLES

The present disclosure will be described in greater detail by way of specific examples. The following examples are offered for illustrative purposes only and are not intended to limit the disclosure in any manner.

Example 1. Materials and Methods

1.1 Study Subjects

This study included mothers enrolled in the CHARGE study (Childhood Autism Risks from Genetics and Environment) at the MIND Institute at UC Davis [19]. The CHARGE study participants in this study included mothers with children diagnosed with ASD (n=246) and with children selected from the general population (typically developing, TD; n=149). We used the recruitment, eligibility, and psychometric assessment procedures as previously described [7, 19]. ASD diagnosis was verified at the MIND Institute according to the Diagnostic and Statistical Manual of Mental Disorders-5 (DSM-5)[20]. All the procedures were approved by the California Committee for the Protection of Human Subjects and institutional review boards at UC Davis and UC Los Angeles. Prior to participation, subjects provided written informed consent in either English or Spanish. The demographic information related to these samples is shown in Table 1.

1.2 Sample Collection and Preparation

Blood was collected in citrate dextrose (BD Diagnostic) and plasma was separated, coded, aliquoted, and stored at −80° C. Prior to use, samples were thawed and centrifuged at 13,000 RPM for 10 minutes.

1.3 Fetal Brain Antigen Preparation

Tissue processing was done as previously described [8]. Briefly, we used embryonic 152 day-old fetal rhesus macaque brain (FMB) that was supplied by the California National Primate Research Center. The FMB was mechanically homogenized with buffer using a Polytron 3000 homogenizer (Brinkman), sonicated for 3 minutes, and centrifuged for 10 minutes at 3,000×g. The supernatant was then collected, concentrated via ultrafiltration, and measured for its protein content via bicinchoninic acid assay (BCA).

1.4 Prep Cell

Protein fractionation was performed as described previously [8]. Briefly, 40 mg of FMB was electrophoresed and separated by molecular weight using a Prep Cell apparatus (Bio Rad, Hercules, CA) on a 10% poly-acrylamide gel for 17 hours at 12 watts. Protein fractions were collected at 5-minute intervals at a flow rate of 0.75 ml/min. A total of 110 fractions were obtained, concentrated to 5 mg/ml by ultrafiltration, and probed by western blot (WB) to determine molecular weight and antigen reactivity (FIGS. 1A-1D). Ponceau staining confirmed protein enrichment and fractions with a range of approximately 5 kDa per/fraction. Fraction #12 contained proteins between 37-45 kDa and was therefore selected to use for antigen identification (FIGS. 2A-2E).

1.5 Western Blot

To test autoantibody reactivity to FMB Fraction #12 that contained proteins between 37-45 kDa, the fraction was probed with maternal plasma samples as described previously (FIG. 1D) [8]. In summary, 200 μg of protein were denatured by heating at 100° C. for 10 min in SDS buffer and separated on a 12% SDS-PAGE gel at 200V for 1 hour. Proteins were transferred to a 0.2 μm nitrocellulose membrane overnight (10V for 16 hours) at 4° C. To confirm the transfer, the membrane was stained with Ponceau dye and cut into 3 mm strips that were labeled and blocked with 1% casein buffer. Plasma samples were then diluted (1:400), added to the strips, incubated for 1.5 hours at RT followed by five washes, and incubated with 1:20,000 goat anti-human IgG-HRP for 30 minutes. After five washes, detection was performed by adding 800 μl of Super Signal substrate and strips were placed on a glass plate to be imaged using the FluoroChem 8900 imager. Images were scored as 0 if negative and 1 if positive.

1.6 Two-Dimensional (2-D) Gel Electrophoresis

Protein fractions that were targeted by maternal autoantibodies were separated by 2-D electrophoresis as described previously [8]. Briefly, 300 μg of the protein fraction in the 30-40 kDa range were labeled with Cy2 (GE Life Sciences, Pittsburgh, PA, USA) in preparation for 2-D electrophoresis (all gels were done in duplicate). First, 15 μg of each sample was separated by its isoelectric point by using 3-10 isoelectric focusing strips (GE Healthcare, Piscataway, NJ, USA). The strips were then loaded onto 2 10.5% polyacrylamide gels (GE Healthcare) for second dimension electrophoresis. Images were captured using Quant software (version 6.0, GE Healthcare). One of the gels was transferred to nitrocellulose membrane to assay for maternal plasma reactivity to bands near 37-39 kDa, but unreactive to, GDA, LDHA/B, and YBX1 by WB. The resulting positive spots were mapped back to the Cy2 stained duplicate 2-D gel, picked from the gel, and digested with trypsin (Promega, Madison, WI, USA) in preparation for Mass spectrometry analysis.

1.7 Mass Spectrometry

Mass spectrometric analysis was performed as described in our previous report [8]. The digested peptides were desalted (Zip-tip C18, Millipore, Billerica, MA, USA)) and spotted on the MALDI plate (model ABI 01-192-6-AB). The ABI 4700 mass spectrometer (Applied Biosystems, Framingham, MA) was used to obtain MALDI-TOF MS and TOF/TOF tandem MS/MS data. The obtained peptide mass and the associated fragmentation spectra were analyzed using a GPS Explorer workstation equipped with MASCOT search engine (Matrix Science, Boston, MA, USA) and used to perform a BLAST search on the NCBI. Candidates with either protein score confidence interval (C.I. %) or Ion C.I. % of greater than 95 were considered positive (Table 1).

The top 4 commercially available antigens identified by mass spectrometry with a 100 C.I. were selected for further evaluation. To evaluate antibody reactivity against our top hits including NSE, NNE, ALDOC, and CKB, 2 μg protein of recombinant protein (Novus Biologicals, Littleton, CO) were probed with diluted maternal plasma (1:800) by WB as described previously.

1.8 Enzyme Linked Immunosorbent Assay (ELISA)

Once NSE was identified as a viable antigenic candidate by WB, we evaluated a larger sample set for NSE reactivity using an ELISA method. We tested plasma from 418 mothers enrolled in the CHARGE study with at least one child with ASD (n=232) or control samples from mothers of typically developing children (TD; n=186). Microtiter plates were coated with 100 μl of NSE (Novus Biologicals, Littleton, CO) at 2 μg/ml in carbonate coating buffer pH 9.6, incubated overnight at 4° C., washed four times with PBST 0.05%, and blocked with 2% Super Block (Thermo Scientific, Rockford, IL) for 1 hour at room temperature (RT). The plasma samples were diluted 1:500 and run in duplicate. Following dilution, 100 μl of diluted sample was added to each well, incubated for 1.5 hours, washed 4×, then incubated with 1:10,000 goat anti-human IgG-HRP IgG (Kirkegaard & Perry Laboratories, Inc., Gaithersburg, MA) for 1 hour. The plates were then washed and detection was performed by adding 100 μl of BD optEIA liquid substrate for ELISA (BD Biosciences, San Jose, CA). After 4 minutes, the reaction was stopped with 50 μl of 2N HCl. The absorbance was measured at 490-450 nm using an iMark Microplate Absorbance Reader (Biorad, Hercules, CA, USA).

1.9 Receiver Operating Characteristic (ROC) Curve

For the ELISA assay, positive cutoff values for reactivity to NSE were determined using a ROC curve. The ROC curve was created by plotting the true positive rate against the false positive rate at various threshold settings. We therefore created our curve using seven positive samples (labeled as +) from mothers that have a child with ASD and were positive by WB (true positive samples) along with the test samples. By using the positive samples as the reference event, the cutoff has greater specificity (less false positives) although sacrificing some sensitivity (limit of detection). The ROC plots sensitivity versus 1−Specificity for each value creating an Area Under the Curve (AUC) that is a representation of the accuracy of the test. Youden's index was used to calculate the cutoff [21, 22].

1.10 Microarray Screening

The full NSE sequence (NP_001966.1) was obtained from NCBI and translated into a library of contiguous 15-mer peptides with a peptide-peptide overlap of 14 amino acids (aa) onto microarray slides. The discovery peptide microarrays were synthesized by PEPperPRINT as previously described [23] whereby the targeted 15-mer peptide sequences are directly printed onto a glass slide in duplicate using solid-phase Fmoc chemistry (PEPperPRINT, Heidelberg, Germany). Peptides derived from human influenza hemagglutinin (HA) (YPYDVPDYAG) and the Polio vaccine (KEVPALTAVETGAT) were also included as positive controls.

To test for antibody reactivity against the printed peptides, we probed the arrays with plasma from mothers enrolled in the CHARGE study (ASD=27 and TD=22) according to the manufacturer's instructions. The microarray slides were first incubated with standard buffer (PBS containing 0.05% Tween 20, pH 7.4) for 10 minutes and then blocked for 45 minutes at RT (Rockland Blocking Buffer MB-070; Rockland Immunochemicals Inc). The slides were then incubated overnight shaking at 4° C. with individual maternal plasma samples diluted 1:250 in staining buffer followed by 3 washes in standard buffer. For signal detection, the slides were incubated for 30 minutes at RT with goat anti-human IG (H+L)-DyLight649 (Rockland Immunochemicals Inc.) at a dilution of 1:5000 in staining buffer (standard buffer with 10% blocking buffer). Following secondary antibody incubation, the microarrays were imaged using the GenePix 4000B Microarray Scanner (Molecular Devices, Sunnyvale, California).

Fluorescence signal quantification of spot intensities (FI) and peptide annotation was done using PepSlide Analyser software (PEPperPRINT) based on manufacturer's recommendations. The data pre-processing methodology was performed as reported in previous peptide microarray studies. Briefly, net fluorescence intensities (FI) were calculated using the correction method reported by Zue et al [24, 25]. A 3×2 window was set for each spot and the median of the six spots was used as the "neighborhood background" for the central spot. In order to normalize the net Fluorescence intensities (FI) a 3×1 "slide window" was set to each spot, and the median of the three was used as the normalized signal for the central spot [24, 25]. The corrected net intensity was calculated by subtracting the corrected background from the normalized signal. If the background signal was higher in the background compared to the spot (negative FI), the signal was set to 1 as reported in similar studies [26, 27].

Finally, after background correction and the signal normalization, the corrected net signal was obtained by calculating the median of the duplicates and the coefficient of variation was calculated. Samples that had a CV higher that 50% were flagged and corrected. Values under 200 FI were treated as negative due to non-specific binding, and only sequences with values over 200 were considered positive for statistical analysis [26, 27]

1.11 Statistical Analysis

In order to thoroughly examine the data for sequences that were significantly different between diagnostic groups and to identify epitopes that are specific for a given group (TD or ASD), we used two different analytic methods: 1) T-test—a parametric test that allowed us to compare two independent samples through mean differences and assume normal distribution of the data, and 2) Significance Analysis of Microarrays (SAM)—a permutation-based approach that measures the strength of the relationship between epitope expression and the response variable, in this case an ASD and TD diagnosis. The SAM score is directly proportional to the significance of the relationship of the data (Maximum score=2). T-test was performed using XLSTAT 2015.1 software (Addinsoft, Paris, France), and SAM analysis was run using an R statistical computing environment. In addition, we compared the prevalence of epitope reactivity between ASD vs TD groups by Fisher exact test. Differences were considered significant if $p<0.05$. Odds Ratio (OR 95% C.I) were also calculated for significant sequences using GraphPad Prism software (GraphPad Software, San Diego, CA).

Example 2. Antigen Identification

Figure 1D:
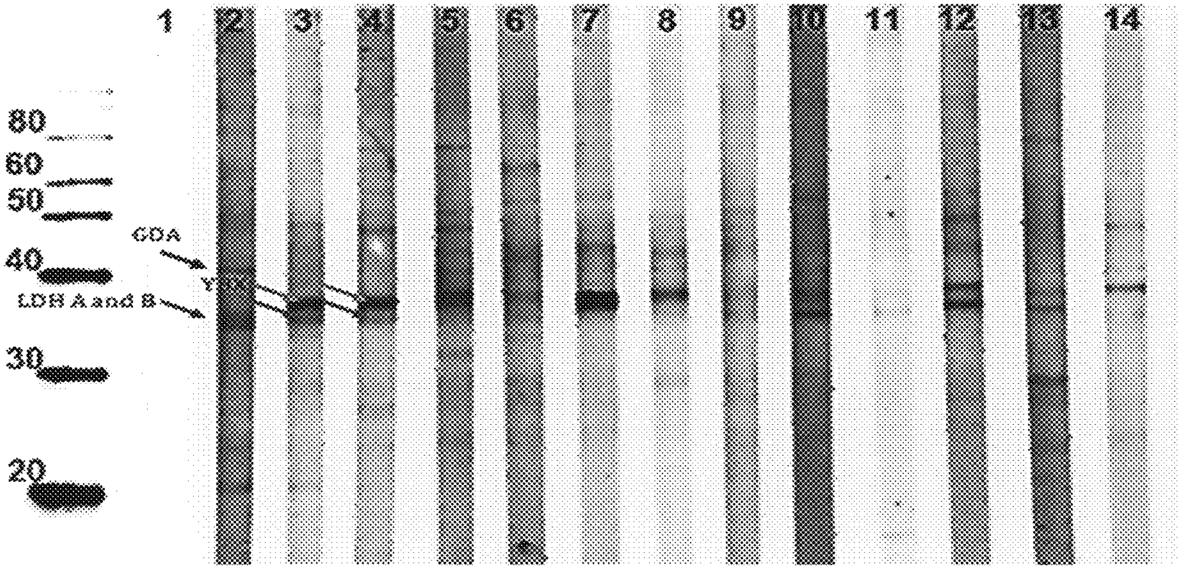

Fetal monkey brain (FMB) brain was separated by molecular weight into 110 fractions, and fraction #12 containing proteins with a molecular weight of 37-45 kDa (FIGS. 1B and 1C) was analyzed on pairs of 2-D gels/western blots (FIGS. 2A-2E). One gel was transferred to nitrocellulose membrane and used to verify autoantibody reactivity to proteins between 37-45 kDa by mothers of children with ASD (FIGS. 1B and 1C) that were negative for the previously described autoantigens in that molecular weight range (GDA, LDHA, LDHB, and YBX1) by WB (FIG. 1D). Multiple spots were observed, and all identified spots were collected from the second matching 2-D gel for mass spectrometric analysis (FIGS. 2A-2E). Proteins near 37-45 kDa with a 100% CI were selected for verification, and detailed mass spectrometry results for the verified antigens are listed in Table 2.

The top 4 commercially available proteins recognized by maternal autoantibodies with a 100% CI were selected for further evaluation including Neuron-Specific Enolase (NSE), Non-Specific Enolase (NNE), Fructose-Bisphosphate Aldolase C (ALDOC) and Creatinine Kinase B (CKB). Each of these proteins were tested to evaluate maternal autoantibody reactivity against individual antigens using recombinant proteins. NSE was subsequently identified by the maternal samples as corresponding to the 37-45 kDa bands, was recognized with the greatest specificity in the tested samples, and was therefore chosen as the most likely candidate for an additional MAR ASD target autoantigen.

Example 3. Antigen Verification

NSE was identified by mass spectrometry as a potential target of the maternal autoantibodies and, based on its critical role in neurodevelopment, we chose to further evaluate NSE as a potential MAR ASD biomarker. Recombinant NSE was used to verify maternal autoantibody reactivity first by WB followed by ELISA. Reactivity was observed in 26 of the 232 mothers that had a child with ASD (6.2%) and in 21 of 186 mothers that have a typically developing child (TD, 5%) suggesting that NSE alone is not a MAR ASD biomarker. Therefore, we utilized an approach similar to that used for the seven previously-described MAR autoantigens to probe the samples for differential epitope recognition between ASD and TD groups.

Example 4. Epitope Mapping

The full NSE sequence (NP_001966.1) was translated into 434 different 15-mer peptides with 14 aa overlap and printed in duplicate onto a glass microarray, which then were probed with diluted plasma from mothers from the ASD and control groups. After the data pre-processing steps, we divided the samples into two categories based on reactivity by ELISA (Positive: samples with antibodies against NSE; Negative: samples negative to NSE in its native form but might have reactivity to cryptic epitopes) for statistical analysis. For the ELISA (+) samples, we found 16 sequences that were ASD-specific (0% TD) and 5 sequences recognized by antibodies from both groups (FI>200). From the 16 ASD specific sequences, 4 sequences were statistically significant using both the t-test and SAM t-test (Table 3). DVAASEFYRDGKYDL (SEQ ID NO:1) (p=0.047; SAM score 1.49), IEDPFDQDDWAAWSK (SEQ ID NO:2) (p=0.049, SAM score 1.49), ERLAKYNQLMRIEEE (SEQ ID NO:3) (p=0.045; SAM score 1.57), and RLAKYNQLMRIEEEL (SEQ ID NO:4) (p=0.017; SAM score 1.82).

Figure 3:
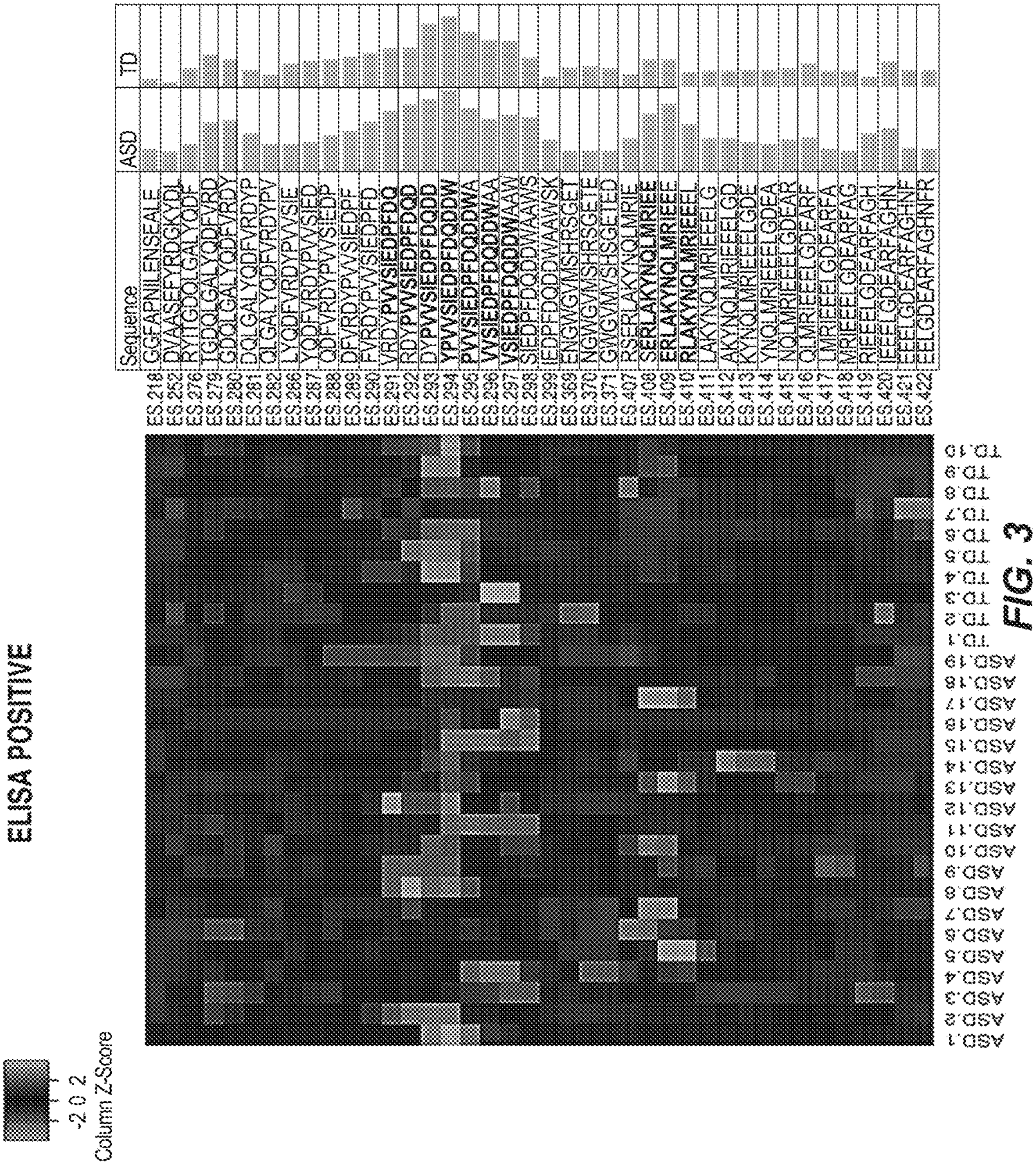
FIG. 3. Heat map of sequences with average reactivity (FI) over 50 from ELISA positive samples. Samples were considered positives if FI >200. Letters in red illustrate the amino acid residues that are part of the main epitope in ES 293-297, and ES 408-410 illustrate the amino acid sequences recognized by the ASD group only. On the right, a histogram represents the FI reactivity. Abbreviations: ES, Epitope Sequence: ASD, Autism Spectrum Disorders; TD, Typically Developing; F1, Fluorescence Intensity.
Figure 4:
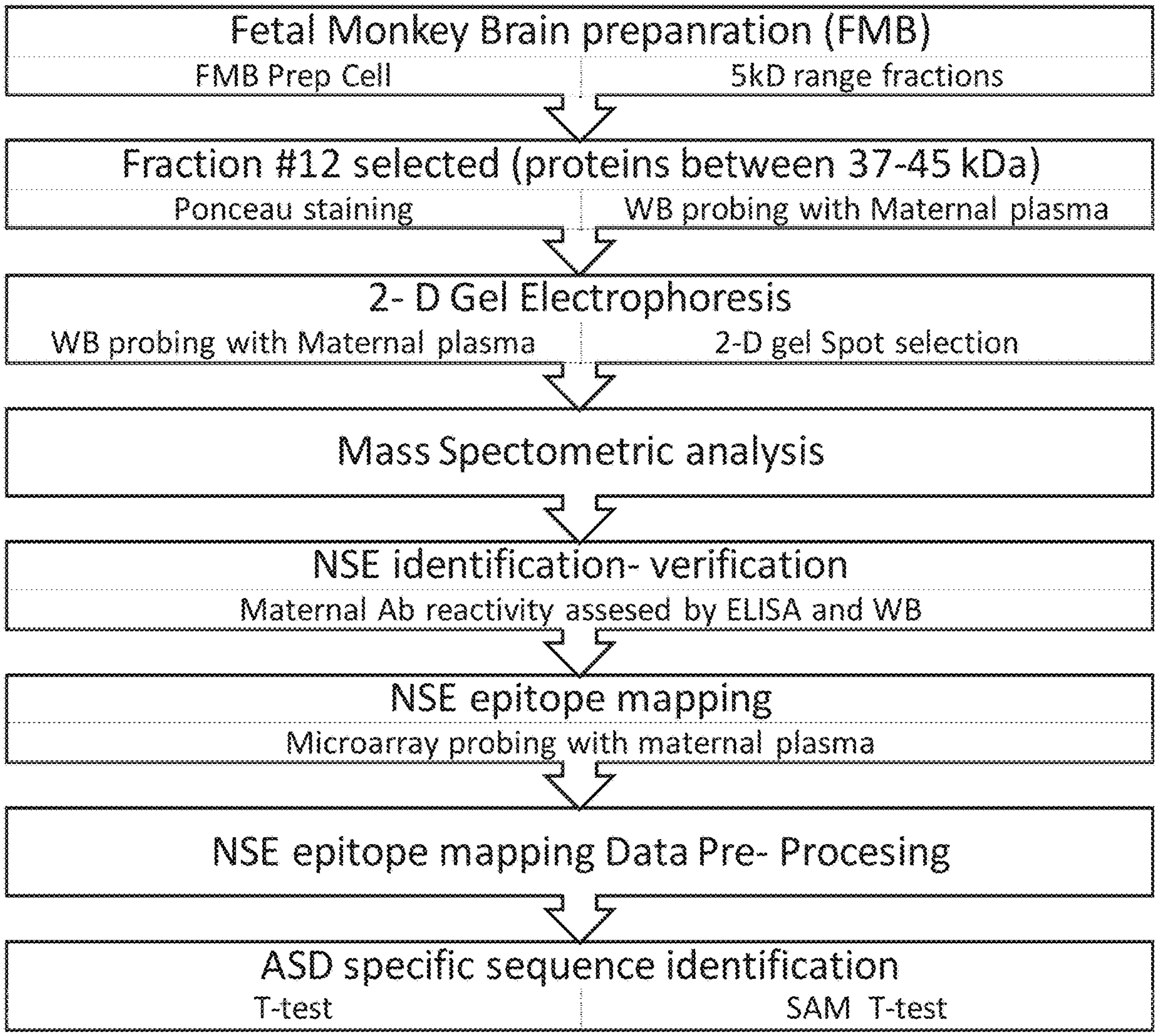
FIG. 4. Workflow representation of the methods used in the Examples. The first three steps were to identify the proteins between 37-45 kDa that were reactive with maternal plasma from mothers that have a child with ASD. The fourth step leads to the identification of the targeted antigens (including NSE). The next steps show the antigen characterization in the context of MAR ASD biomarker.
Figure 5:
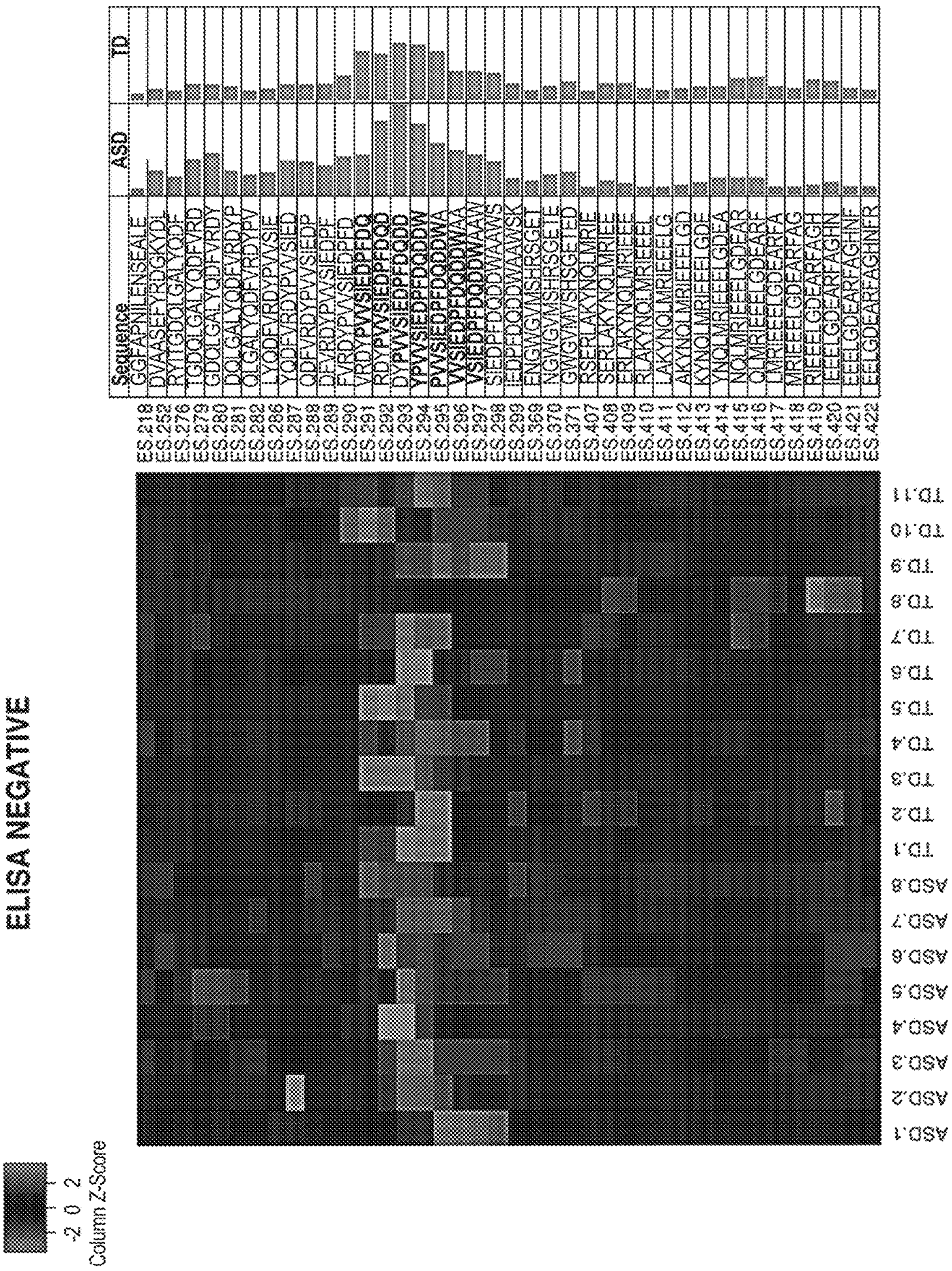
FIG. 5. Heat map of sequences with average reactivity (FI) over 50 from ELISA negative samples. Samples were considered positive if FI >200. Amino acid residues that are part of the main epitope are highlighted in red. On the right, a histogram represents the FI reactivity. Abbreviations: ES, Epitope Sequence; ASD, Autism Spectrum Disorders; TD, Typically Developing; FI, Fluorescence Intensity.

In addition, to evaluate the association of the epitope sequences with a given group we used a Fisher exact test and found no significant differences, likely due to our small sample size. Instead, we calculated odds ratios (ORs) with 95% confidence intervals (95% CIs) for each individual peptide. We found that all ASD specific sequences had an OR above three, with SERLAKYNQLMRIEE (SEQ ID NO:6) (OR 10.1, CI 95% 0.5094 to 200.7) and ERLAKYNQLMRIEEE (SEQ ID NO:3) (OR 12.6, CI 95% 0.6408 to 247.7) being the two epitopes with the highest OR (FIG. 3). As noted above, we found five continuous epitope sequences that were recognized by plasma from both sample groups, suggesting a large immunodominant epitope that includes the printed sequences DYPVVSIEDPFDQDD (SEQ ID NO:7), YPVVSIEDPFDQDDW (SEQ ID NO:8), PVVSIEDPFDQDDWA (SEQ ID NO:9), VVSIEDPFDQDDWAA (SEQ ID NO:10), and VSIEDPFDQDDWAAW (SEQ ID NO: 11) (Table 3). As is noted in FIG. 3, the sequences highlighted in red illustrate the conserved amino acids that were recognized by the antibodies in each of the five different peptide epitopes. Reactivity to the large main immunodominant epitope was also observed in ELISA (−) samples, suggesting that it is a mimotope largely recognized by the general population (Table 4). Interestingly, we also found one ASD-specific epitope sequence, QDFVRDYPVVSIEDP (p=0.054, SAM score 1.97, OR 12.6, CI 95% 0.6408 to 247.7; SEQ ID NO:23), that was recognized by the ELISA (−) samples, suggesting that it is likely unreactive to the native structure of NSE, and more likely binding to a cryptic determinant (Table 4).

Example 5. Bioinformatics

In order to have a better understanding of the potential origin of reactivity to the recently identified epitopes, we used the Immune Epitope Database tools (IEDB) to analyze the homology of the epitopes with all the epitopes reported in the IEDB database. We performed a BLAST search with both 90% and 80% sequence homology settings, and found that each of the identified sequences share homology at 90% with the other isoforms of enolase, primarily alpha enolase (Table 5). The DYPVVSIEDPFDQDD (SEQ ID NO:7) and DFVRDYPVVSIEDPF (SEQ ID NO:16) epitopes each had 90°/% homology with the Protein ORF73 from Human gamma-herpesvirus 8 (Mononucleosis causing agent), and DVAASEFYRDGKYDL (SEQ ID NO:1) had 90% homology with the Outer surface protein A from *Borrelia burgdorferi* (Lyme disease causing agent). Other sequences had 80% homology with peptides from different organisms including genome polyprotein from Hepatitis C virus, virion-packaging protein UL25 from Human beta herpesvirus 6B, Alt a 6 from *Alternaria* alternate, ATP-dependent RNA helicase RhlB from *Vibrio cholerae* and Protein X from Hepatitis B virus. (Table 5).

REFERENCES

1. Baio, J., et al., *Prevalence of Autism Spectrum Disorder Among Children Aged* 8 *Years—Autism and Developmental Disabilities Monitoring Network,* 11 *Sites, United States,* 2014. MMWR Surveill Summ, 2018. 67(6): p. 1-23 DOI: 10.15585/mmwr.ss6706a1.
2. al-Haddad, B. J. S., et al., *Long-term Risk of Neuropsychiatric Disease After Exposure to Infection In UteroNeuropsychiatric Disease After Exposure to Infection In UteroNeuropsychiatric Disease After Exposure to Infection In Utero*. JAMA Psychiatry, 2019. 76(6): p. 594-602 DOI: 10.1001/jamapsychiatry.2019.0029.
3. Bai, D., et al., *Association of Genetic and Environmental Factors With Autism in a* 5*-Country CohortGenetic and Environmental Associations With Autism in a* 5*-Country CohortGenetic and Environmental Associations With Autism in a* 5*-Country Cohort*. JAMA Psychiatry, 2019 DOI: 10.1001/jamapsychiatry.2019.1411.
4. Hallmayer, J., et al., *Genetic heritability and shared environmental factors among twin pairs with autism*. Arch Gen Psychiatry, 2011. 68(11): p. 1095-102 DOI: 10.1001/archgenpsychiatry.2011.76.
5. Kim, Y. S. and B. L. Leventhal, *Genetic epidemiology and insights into interactive genetic and environmental effects in autism spectrum disorders*. Biol Psychiatry, 2015. 77(1): p. 66-74 DOI: 10. 1016/j.biopsych.2014.11.001.
6. Braunschweig, D., et al., *Autism: maternally derived antibodies specific for fetal brain proteins*. Neurotoxicology, 2008. 29(2): p. 226-31 DOI: 10.1016/j.neuro.2007.10.010.
7. Braunschweig, D., et al., *Behavioral correlates of maternal antibody status among children with autism*. J Autism Dev Disord, 2012. 42(7): p. 1435-45 DOI: 10.1007/s10803-011-1378-7.
8. Braunschweig, D., et al., *Autism-specific maternal autoantibodies recognize critical proteins in developing brain*. Transl Psychiatry, 2013. 3: p. e277 DOI: 10.1038/tp.2013.50.
9. Braunschweig, D., et al., *Maternal autism-associated IgG antibodies delay development and produce anxiety in a mouse gestational transfer model*. J Neuroimmunol, 2012. 252(1-2): p. 56-65 DOI: 10.1016/j.jneuroim.2012.08.002.
10. Camacho, J., et al., *Embryonic intraventricular exposure to autism-specific maternal autoantibodies produces alterations in autistic-like stereotypical behaviors in offspring mice*. Behav Brain Res, 2014. 266: p. 46-51 DOI: 10.1016/j.bbr.2014.02.045.
11. Jones, K. L., et al., *Autism-specific maternal autoantibodies produce behavioral abnormalities in an endogenous antigen-driven mouse model of autism. Mol Psychiatry,* 2018 DOI: 10.1038/s41380-018-0126-1.
12. Singer, H. S., et al., *Prenatal exposure to antibodies from mothers of children with autism produces neurobehavioral alterations: A pregnant dam mouse model*. J Neuroimmunol, 2009. 211(1-2): p. 39-48 DOI: 10.1016/j.jneuroim.2009.03.011.
13. Bauman, M. D., et al., *Maternal antibodies from mothers of children with autism alter brain growth and social behavior development in the rhesus monkey*. Transl Psychiatry, 2013. 3: p. e278 DOI: 10.1038/tp.2013.47.
14. Martin, L. A., et al., *Stereotypies and hyperactivity in rhesus monkeys exposed to IgG from mothers of children*

*with autism*. Brain Behav Immun, 2008. 22(6): p. 806-16 DOI: 10.1016/j.bbi.2007.12.007.

15. Edmiston, E., et al., *Identification of the antigenic epitopes of maternal autoantibodies in autism spectrum disorders*. Brain Behav Immun, 2017 DOI: 10.1016/j.bbi.2017.12.014.
16. Fukano, K. and K. Kimura, *Measurement of enolase activity in cell lysates*. Methods Enzymol, 2014. 542: p. 115-24 DOI: 10.1016/b978-0-12-416618-9.00006-6.
17. Isgro, M. A., P. Bottoni, and R. Scatena, *Neuron-Specific Enolase as a Biomarker: Biochemical and Clinical Aspects*. Adv Exp Med Biol, 2015. 867: p. 125-43 DOI: 10.1007/978-94-017-7215-0-9.
18. Haque, A., et al., *New Insights into the Role of Neuron-Specific Enolase in Neuro-Inflammation, Neurodegeneration, and Neuroprotection*. Brain Sci, 2018. 8(2) DOI: 10.3390/brainsci8020033.
19. Hertz-Picciotto, I., et al., *The CHARGE study: an epidemiologic investigation of genetic and environmental factors contributing to autism*. Environ Health Perspect, 2006. 114(7): p. 1119-25.
20. Associateion, A. P., *Diagnostic and Statistical Manual of Mental Disorders* (DSM-5). 5 ed. 2013: American Psychiatric Association.
21. Fluss, R., D. Faraggi, and B. Reiser, *Estimation of the Youden Index and its Associated Cutoff Point*. Biometrical Journal, 2005. 47(4): p. 458-472 DOI: 10.1002/bimj.200410135.
22. Hajian-Tilaki, K., *Receiver Operating Characteristic (ROC) Curve Analysis for Medical Diagnostic Test Evaluation*. Caspian journal of internal medicine, 2013. 4(2): p. 627-635.
23. Schirwitz, C., et al., *Sensing immune responses with customized peptide microarrays*. Biointerphases, 2012. 7(1-4): p. 47 DOI: 10.1007/s13758-012-0047-5.
24. Zhu, X., M. Gerstein, and M. Snyder, *ProCAT: a data analysis approach for protein microarrays*. Genome Biology, 2006. 7(11): p. R110 DOI: 10.1186/gb-2006-7-11-r110.
25. Duarte, J., et al., *Protein Function Microarrays: Design, Use and Bioinformatic Analysis in Cancer Biomarker Discovery and Quantitation, in Bioinformatics of Human Proteomics*, X. Wang, Editor. 2013, Springer Netherlands: Dordrecht. p. 39-74.
26. Hecker, M., et al., *Computational analysis of high-density peptide microarray data with application from systemic sclerosis to multiple sclerosis. Autoimmunity Reviews,* 2012. 11(3): p. 180-190 DOI: https://doi.org/10.1016/j.autrev.2011.05.010.
27. Hecker, M., et al., *High-Density Peptide Microarray Analysis of IgG Autoantibody Reactivities in Serum and Cerebrospinal Fluid of Multiple Sclerosis Patients*. Mol Cell Proteomics, 2016. 15(4): p. 1360-80 DOI: 10.1074/mcp.M115.051664.
28. Zhou, J. J., et al., *Neuron specific enolase gene silencing suppresses proliferation and promotes apoptosis of lung cancer cells in vitro*. Nan Fang Yi Ke Da Xue Xue Bao, 2011. 31(8): p. 1336-40.
29. Liu, X., et al., *Knockdown of neuron specific enolase suppresses the proliferation and migration of NCI H*209 cells. Oncology Letters, 2019 DOI: 10.3892/ol.2019.10797.
30. Isgrò, M. A., P. Bottoni, and R. Scatena, *Neuron-Specific Enolase as a Biomarker: Biochemical and Clinical Aspects, in Advances in Cancer Biomarkers: From biochemistry to clinic for a critical revision*, R. Scatena, Editor. 2015, Springer Netherlands: Dordrecht. p. 125-143.
31. Warren, R. P., et al., *Detection of maternal antibodies in infantile autism*. J Am Acad Child Adolesc Psychiatry, 1990. 29(6): p. 873-7 DOI: 10.1097/00004583-199011000-00005.
32. Zimmerman, A. W., et al., *Maternal antibrain antibodies in autism*. Brain Behav Immun, 2007. 21(3): p. 351-7 DOI: 10.1016/j.bbi.2006.08.005.
33. Brennan, C., et al., *Modulation of enzyme activity by antibody binding to an alkaline phosphatase-epitope hybrid protein*. Protein Eng, 1994. 7(4): p. 509-14.
34. Cinader, B. and K. J. Lafferty, *MECHANISM OF ENZYME INHIBITION BY ANTIBODY. A STUDY OF THE NEUTRALIZATION OF RIBONUCLEASE*. Immunology, 1964. 7(4): p. 342-362.
35. Lu, C., et al., *The binding sites for competitive antagonistic, allosteric antagonistic, and agonistic antibodies to the I domain of integrin LFA-1*. J Immunol, 2004. 173(6): p. 3972-8 DOI: 10.4049/jimmunol.173.6.3972.
36. Mayes, P. A., K. W. Hance, and A. Hoos, *The promise and challenges of immune agonist antibody development in cancer*. Nature Reviews Drug Discovery, 2018. 17: p. 509 DOI: 10.1038/nrd.2018.75.
37. Martinez-Cerdeño, V., et al., *Prenatal Exposure to Autism-Specific Maternal Autoantibodies Alters Proliferation of Cortical Neural Precursor Cells, Enlarges Brain, and Increases Neuronal Size in Adult Animals*. Cerebral Cortex, 2014. 26(1): p. 374-383 DOI: 10.1093/cercor/bhu291.
38. Vita, R., et al., *The Immune Epitope Database (IEDB)*: 2018 update. Nucleic Acids Res, 2019. 47(D1): p. D339-d343 DOI: 10.1093/nar/gky1006.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

TABLE 1

Demographics of study population. Illustrates the mean maternal age at birth of child and mean age of child at time of sample collection.

| Diagnosis | Number of Subjects | Maternal Age at birth of child (yrs) | SD | Max | Min | Child Age at time of draw (mo) | SD | Max | Min |
|---|---|---|---|---|---|---|---|---|---|
| ASD | 28 | 30 | 6 | 40 | 19 | 49 | 9 | 60 | 31 |
| ELISA+ | 20 | | | | | | | | |
| ELISA− | 8 | | | | | | | | |

TABLE 1-continued

Demographics of study population. Illustrates the mean maternal age at birth of child and mean age of child at time of sample collection.

| Diagnosis | Number of Subjects | Maternal Age at birth of child (yrs) | SD | Max | Min | Child Age at time of draw (mo) | SD | Max | Min |
|---|---|---|---|---|---|---|---|---|---|
| TD | 22 | 31 | 4 | 36 | 20 | 46 | 8 | 60 | 25 |
| ELISA+ | 11 | | | | | | | | |
| ELISA− | 11 | | | | | | | | |

Abbreviations: ASD, Autism Spectrum Disorders; TD, Typically Developing, SD, Standard Deviation, Max, Maximum age, Min, Minimum age.

[a]Subjects from Childhood Autism Risk from Genetics and the Environment (CHARGE) study.

TABLE 2

Figures 2A, 2B, 2C:
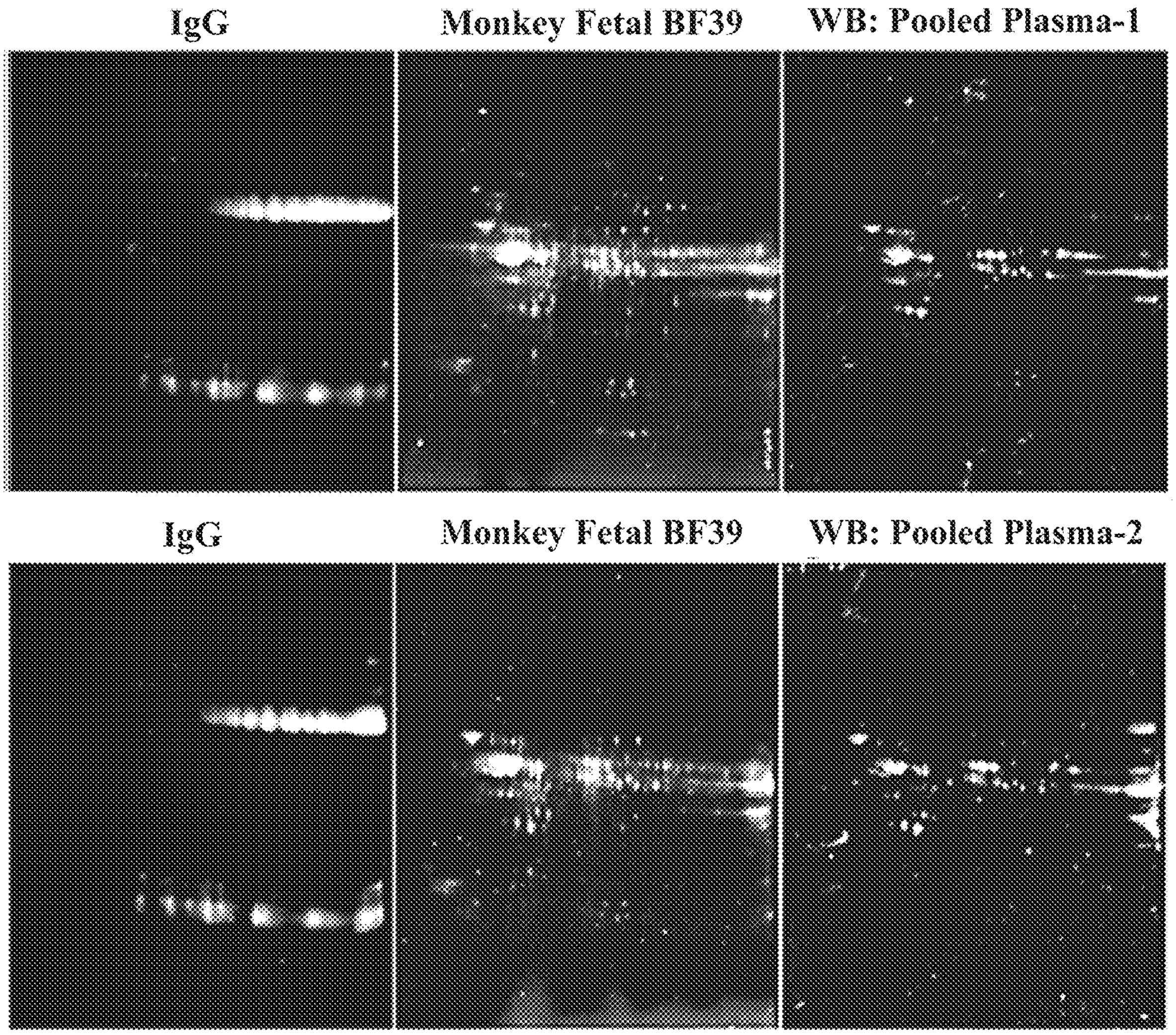
FIGS. 2A-2E. Two-dimensional (2-D) gel electrophoresis and antigen selection for mass spectrometry.
Figure 2D:
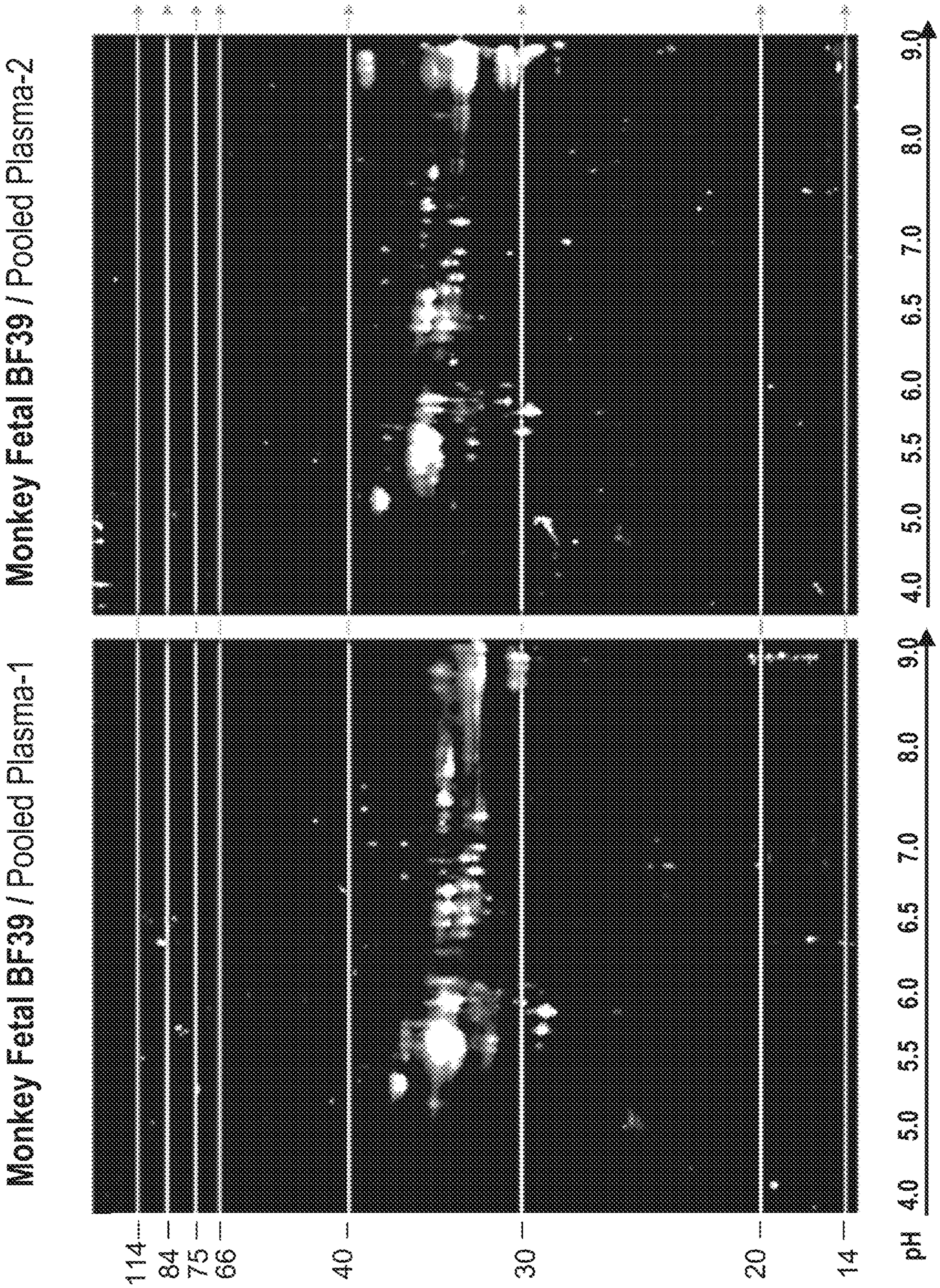
Figure 2E:
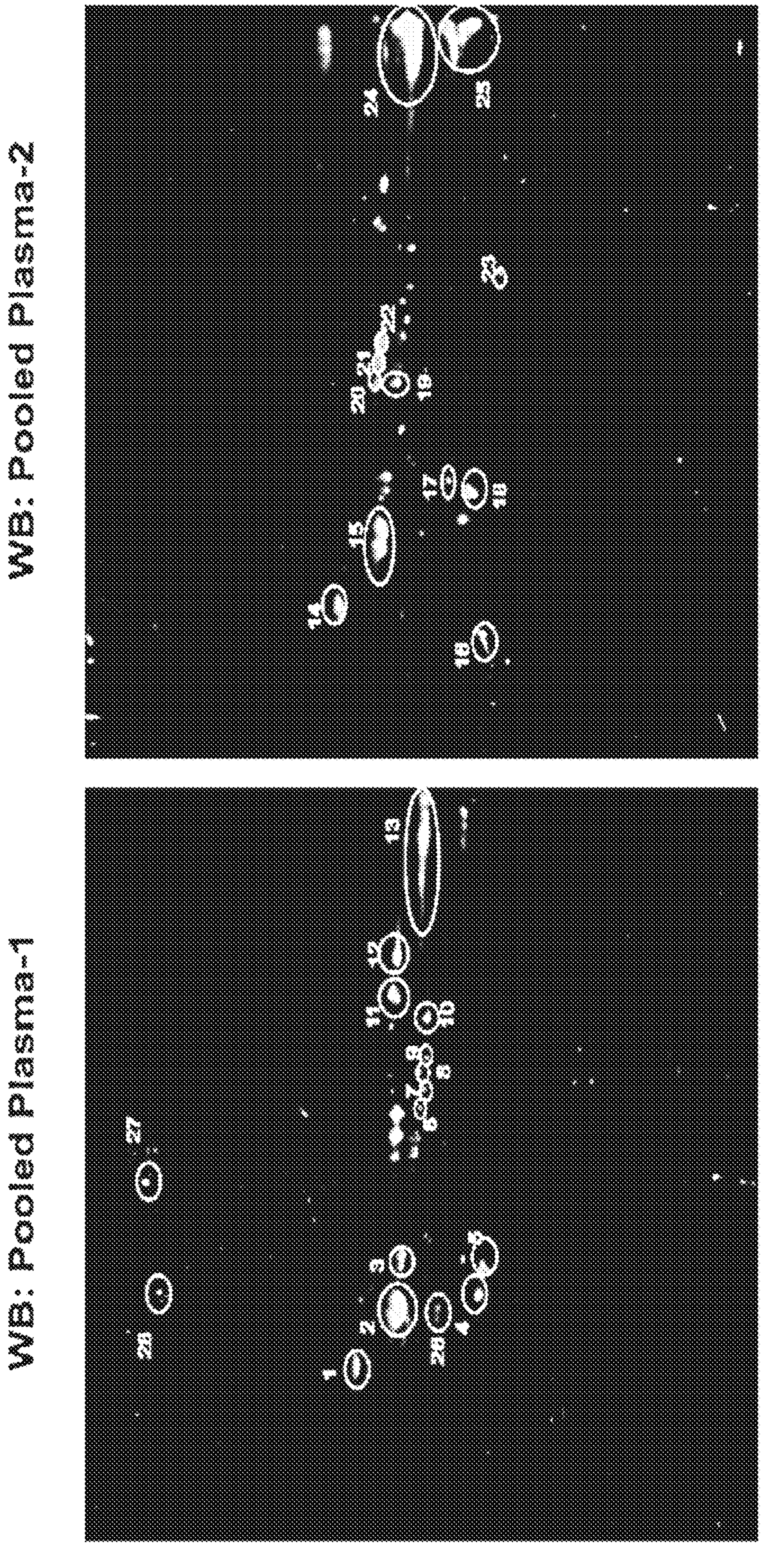

Summary of the mass spectroscopy results from each spot selected in FIG. 2E

| Plasma Sample | Spot Number | Protein | Accession Number | Peptide Counts | Protein Score (% CI) | MW (Dalton) |
|---|---|---|---|---|---|---|
| Sample #1 | 1 | Gamma Enolase Isoform 2 | gi\|297261688 | 20 | 100 | 42654.6 |
| | 2 | Actin | gi\|297273827 | 18 | 100 | 41743.8 |
| | 3 | Creatine Kinase B-Type Isoform 1 | gi\|109103537 | 23 | 100 | 42625.3 |
| | 4 | Guanine Nucleotide Binding Protein | gi\|297288022 | 3 | 100 | 23727.5 |
| | 5 | Guanine Nucleotide Binding Protein | gi\|297288022 | 5 | 100 | 23727.5 |
| | 6 | Fructose-Bisphosphate Aldolase C | gi\|355568354 | 20 | 100 | 39437.3 |
| | 7 | Mitogen-Activated Protein Kinase 1 | gi\|297260645 | 17 | 100 | 40394.8 |
| | 8 | Fructose-Bisphosphate Aldolase C | gi\|355568354 | 19 | 100 | 39437.3 |
| | 9 | Hypothetical Protein EGK 19964 | gi\|355562691 | 21 | 100 | 47145 |
| | 10 | Hypothetical Protein EGK 19964 | gi\|355562691 | 21 | 100 | 47145 |
| | 11 | Septin-2 | gi\|297265280 | 11 | 100 | 45461.3 |
| | 12 | Creatine Kinase S-Type, Mitochondrial Isoform 3 | gi\|355568692 | 4 | 100 | 47479.4 |
| | 13 | 2',3'-cyclic-nucleotide 3'-phosphodiesterase, partial | gi\|355568692 | 23 | 100 | 47474.6 |
| | 26 | Guanine Nucleotide-Binding Protein G(o) Subunit Alpha | gi\|355710206 | 12 | 100 | 35829.6 |
| | 27 | Dynamin-1 | gi\|355567437 | 12 | 100 | 83859.1 |
| | 28 | Probable ATP-Dependent RNA Helicase DDX4 | gi\|297294301 | 12 | 93 | 76918.7 |
| Sample #2 | 16 | Ubiquitin Thioesterase OTUB1 | gi\|109105619 | 12 | 100 | 31485.6 |
| | 17 | Pyridoxal Kinase Isoform 2 | gi\|297287438 | 7 | 77 | 46034.6 |
| | 19 | Septin-2 | gi\|297265280 | 11 | 100 | 45461.3 |
| | 20 | Ornithine Aminotransferase | gi\|297302021 | 10 | 100 | 48430.1 |
| | 21 | Glutamine Synthetase | gi\|19923206 | 14 | 100 | 42037.3 |
| | 22 | Glutamine Synthetase | gi\|19923206 | 12 | 100 | 42037.3 |
| | 23 | Voltage-Dependent Anion-Selective Channel Protein 1 Isoform 2 | gi\|109078605 | 15 | 100 | 30702.6 |
| | 24 | Fructose-Bisphosphate Aldolase A | gi\|355710108 | 12 | 100 | 45253.2 |
| | 25 | Glyceraldehyde-3-Phosphate Dehydrogenase | gi\|306482641 | 12 | 100 | 35959.4 |

The proteins in spot numbers 1, 6, 8, and 21-25 are involved in the glycolysis-gluconeogenesis pathway.

TABLE 3

Summary of significant NSE epitopes recognized by maternal autoantibodies (ELISA positive)

| ES# | SEQUENCE | ASD + N = 19 | TD + N = 10 | p-value T-test | SAM score t-test | Fisher's exact test p-value | Odds Ratio | Con-fidence Interval (95%) | Specific binding |
|---|---|---|---|---|---|---|---|---|---|
| 218 | GGFAPNILENSEALE (SEQ ID NO: 12) | 3 | 0 | 0.163 | 0.94 | 0.532 | 4.455 | 0.2082 to 95.32 | ASD |
| 252 | DVAASEFYRDGKYDL (SEQ ID NO: 1) | 3 | 0 | 0.047 | 1.49 | 0.532 | 4.455 | 0.2082 to 95.32 | ASD |
| 279 | TGDQLGALYQDFVRD (SEQ ID NO: 13) | 5 | 0 | 0.295 | 0.77 | 0.134 | 7.966 | 0.3955 to 160.4 | ASD |
| 280 | GDQLGALYQDFVRDY (SEQ ID NO: 14) | 3 | 0 | 0.101 | 1.23 | 0.134 | 7.966 | 0.3955 to 160.4 | ASD |
| 281 | DQLGALYQDFVRDYP (SEQ ID NO: 15) | 3 | 0 | 0.060 | 1.37 | 0.532 | 4.455 | 0.2082 to 95.32 | ASD |
| 289 | DFVRDYPVVSIEDPF (SEQ ID NO: 16) | 3 | 0 | 0.459 | 0.47 | 0.532 | 4.455 | 0.2082 to 95.32 | ASD |
| 298 | SIEDPFDQDDWAAWS (SEQ ID NO: 17) | 4 | 0 | 0.093 | 1.23 | 0.268 | 6.097 | 0.2958 to 125.6 | ASD |
| 299 | IEDPFDQDDWAAWSK (SEQ ID NO: 2) | 2 | 0 | 0.049 | 1.49 | 0.532 | 3.000 | 0.1309 to 68.76 | ASD |
| 407 | RSERLAKYNQLMRIE (SEQ ID NO: 18) | 3 | 0 | 0.079 | 1.25 | 0.532 | 4.455 | 0.2082 to 95.32 | ASD |
| 408 | SERLAKYNQLMRIEE (SEQ ID NO: 6) | 6 | 0 | 0.107 | 1.25 | 0.068 | 10.110 | 0.5094 to 200.7 | ASD |
| 409 | ERLAKYNQLMRIEEE (SEQ ID NO: 3) | 7 | 0 | 0.045 | 1.57 | 0.063 | 12.600 | 0.6408 to 247.71 | ASD |
| 410 | RLAKYNQLMRIEEEL (SEQ ID NO: 4) | 5 | 0 | 0.017 | 1.82 | 0.134 | 7.966 | 0.3955 to 160.4 | ASD |
| 411 | LAKYNQLMRIEEELG (SEQ ID NO: 19) | 3 | 0 | 0.109 | 1.12 | 0.532 | 4.455 | 0.2082 to 95.32 | ASD |
| 412 | AKYNQLMRIEEELGD (SEQ ID NO: 20) | 3 | 0 | 0.125 | 1.07 | 0.532 | 4.455 | 0.2082 to 95.32 | ASD |
| 413 | KYNQLMRIEEELGDE (SEQ ID NO: 21) | 3 | 0 | 0.231 | 0.81 | 0.532 | 4.455 | 0.2082 to 95.32 | ASD |
| 416 | QLMRIEEELGDEARF (SEQ ID NO: 22) | 3 | 0 | 0.234 | 0.83 | 0.532 | 4.455 | 0.2082 to 95.32 | ASD |
| 293 | DYPVVSIEDPFDQDD (SEQ ID NO: 7) | 6 | 4 | 0.711 | 0.3 | 0.698 | 0.692 | 0.1408 to 3.405 | ASD and TD |
| 294 | YPVVSIEDPFDQDDW (SEQ ID NO: 8) | 8 | 4 | 0.650 | 0.39 | 1.000 | 1.091 | 0.2294 to 5.187 | ASD and TD |
| 295 | PVVSIEDPFDQDDWA (SEQ ID NO: 9) | 5 | 2 | 0.643 | 0.3 | 1.000 | 1.429 | 0.2232 to 9.142 | ASD and TD |
| 296 | VVSIEDPFDQDDWAA (SEQ ID NO: 10) | 4 | 1 | 0.793 | 0.17 | 0.632 | 2.400 | 0.2306 to 24.98 | ASD and TD |
| 297 | VSIEDPFDQDDWAAW (SEQ ID NO: 11) | 4 | 1 | 0.602 | 0.44 | 0.632 | 2.400 | 0.2306 to 24.98 | ASD and TD |

Abbreviations: ES, Epitope Sequence; ASD, Autism Spectrum Disorders; TD, Typically Developing

TABLE 4

| Summary of significant NSE epitopes recognized by maternal autoantibodies (ELISA negative) | | | | | | | | | |
|---|---|---|---|---|---|---|---|---|---|
| ES# | SEQUENCE | ASD + N = 8 | TD + N = 11 | p-value T-test | SAM score t-test | Fisher's exact test p-value | Odds Ratio | Con-fidence Interval (95%) | Specific binding |
| 288 | QDFVRDYPVVSIEDP (SEQ ID NO: 23) | 3 | 0 | 0.054 | 1.97 | 0.069 | 13.360 | 0.5793 to 308.3 | ASD |
| 290 | FVRDYPVVSIFDPFD (SEQ ID NO: 24) | 3 | 1 | 0.174 | 1.34 | 0.275 | 5.400 | 0.4371 to 66.71 | ASD and TD |
| 291 | VRDYPVVSIEDPFDQ (SEQ ID NO: 25) | 4 | 4 | 0.695 | 0.3 | 1.000 | 1.500 | 0.2296 to 9.801 | ASD and TD |
| 292 | RDYPVVSIEDPFDQD (SEQ ID NO: 26) | 5 | 2 | 0.455 | 0.8 | 0.145 | 6.667 | 0.8083 to 54.99 | ASD and TD |
| 293 | DYPVVSIEDPFDQDD (SEQ ID NO: 7) | 6 | 7 | 0.307 | 1.02 | 0.638 | 2.000 | 0.2599 to 15.39 | ASD and TD |
| 294 | YPVVSIEDPIDQDDW (SEQ ID NO: 8) | 5 | 7 | 0.388 | 0.8 | 1.000 | 1.111 | 0.1644 to 7.510 | ASD and TD |
| 295 | PVVSIEDPFDQDDWA (SEQ ID NO: 9) | 4 | 3 | 0.697 | 0.24 | 1.000 | 1.500 | 0.2296 to 9.801 | ASD and TD |
| 296 | VVSIEDPFDQDDWAA (SEQ ID NO: 10) | 4 | 2 | 0.111 | 1.7 | 0.321 | 4.000 | 0.5000 to 32.00 | ASD and TD |
| 297 | VSIEDPFDQDDWAAW (SEQ ID NO: 11) | 2 | 2 | 0.266 | 1.2 | 1.000 | 1.333 | 0.1436 to 12.38 | ASD and TD |

Abbreviations: ES, Epitope Sequence; ASD, Autism Spectrum Disorders; TD, Typically Developing

TABLE 5

| Summary of epitope comparison using the IEDB database | | | | | | |
|---|---|---|---|---|---|---|
| EP# | SEQUENCE | Specific binding | BLAST 90% | | BLAST 80% | |
| 218 | GGFAPNILENSEALE (SEQ ID NO: 12) | ASD | Alpha enolase | Human | NA | NA |
| 252 | DVAASEFYRDGKYDL (SEQ ID NO: 1) | ASD | Outer surface protein A | *B. burgdorferi* | NA | NA |
| 279 | TGDQLGALYQDFVRD (SEQ ID NO: 13) | ASD | Gamma enolase | Human | Genome polyprotein | Hepatitis C virus |
| 280 | GDQLGALYQDFVRDY (SEQ ID NO: 14) | ASD | Gamma, enolase | Human | Genome polyprotein | Hepatitis C virus |
| 281 | DQLGALYQDFVRDYP (SEQ ID NO: 15) | ASD | Gamma enolase | Human | Genome polyprotein | Hepatitis C virus |
| 289 | DFVRDYPVVSIEDPF (SEQ ID NO: 16) | ASD | Protein ORF73 | Human Gamma herpesvirus 8 | Protein ORF73 | Human Gamma herpesvirus 8 |
| 298 | STEDPFDQDDWAAWS (SEQ ID NO: 17) | ASD | Alpha enolase | Human | Serpin H1 | Human |
| 299 | IEDPFDQDDWAAWSK (SEQ ID NO: 2) | ASD | Alpha enolase | Human | Serpin H1 | Human |
| 407 | RSERLAKYNQLMRIE (SEQ ID NO: 18) | ASD | Alpha enolase | Human | Virion-packaging protein UL25 | Human beta herpesvirus 6B |
| 408 | SERLAKYNQLMRIEE (SEQ ID NO: 6) | ASD | Alpha enolase | Human | Alt a 6 | *Alternaria alternata* |
| 409 | ERLAKYNQLMRIEEE (SEQ ID NO: 3) | ASD | Alpha enolase | Human | Alt a 6 | *Alternaria alternata* |

TABLE 5-continued

Summary of epitope comparison using the IEDB database

| EP# | SEQUENCE | Specific binding | BLAST 90% | | BLAST 80% | |
|---|---|---|---|---|---|---|
| 410 | RLAKYNQLMRIEEEL (SEQ ID NO: 4) | ASD | Alpha enolase | Human | ATP-dependent RNA helicase RhlB | *Vibrio cholerae* |
| 411 | LAKYNQLMRIEEELG (SEQ ID NO: 19) | ASD | Alpha enolase | Human | ATP-dependent RNA helicase RhlB | *Vibrio cholerae* |
| 412 | AKYNQLMRIEEELGD (SEQ ID NO: 20) | ASD | Alpha enolase | Human | ATP-dependent RNA helicase RhIB | *Vibrio cholerae* |
| 413 | KYNQIMRIEEELGDE (SEQ ID NO: 21) | ASD | Alpha enolase | Human | Protein X | Hepatitis B virus |
| 416 | QLMRIEEELGDEARF (SEQ ID NO: 22) | ASD | Alpha enolase | Human | Protein X | Hepatitis B virus |
| 293 | DYPVVSIEDPFDQDD (SEQ ID NO: 7) | ASD and TD | Protein ORF73 | Human Gamma herpesvirus 8 | Protein ORF73 | Human Gamma herpesvirus 8 |
| 294 | YPVVSIEDPFDQDDW (SEQ ID NO: 8) | ASD and ID | Alpha enolase | Human | Serpin H1 | Human |
| 295 | PVVSIEDPFDQDDWA (SEQ ID NO: 9) | ASD and TD | Alpha enolase | Human | Immunogenic protein PPE68 | Mycobacterium tuberculosis |
| 296 | VVSIEDPFDQDDWAA (SEQ ID NO: 10) | ASD and TD | Gamma enolase | Human | Serpin H1 | Human |
| 297 | VSHDPFDQDDWAAW (SEQ ID NO: 11) | ASD and TD | Gamma enolase | Human | Serpin H1 | Human |

BLAST sequence homology for 90% and 80% specificity

What is claimed is:

1. An isolated peptide comprising:

(a) an amino acid sequence having at least 80% sequence identity to SEQ ID NO: 1, 2, 4, 5, or 6, or (b) an amino acid sequence having at least 95% sequence identity to SEQ ID NO: 3, wherein the peptide further comprises a label, and wherein the peptide is 15-30 amino acids in length.

2. The peptide of claim 1, wherein the peptide comprises at least 5, 6, 7, 8, 9, 10, 11, 12, 13, 14, or 15 contiguous amino acids of the amino acid sequence of SEQ ID NO: 1, 2, 3, 4, 5, or 6.

3. The peptide of claim 1, wherein the peptide is 15 amino acids in length.

4. The peptide of claim 1, wherein the peptide comprises the amino acid sequence of SEQ ID NO: 1, 2, 3, 4, 5, or 6.

5. The peptide of claim 1, wherein the peptide is a mimotope.

6. The peptide of claim 1, wherein the label is biotin, a fluorescent label, a chemiluminescent label, or a radioactive label.

7. A composition comprising:

(a) a peptide comprising an amino acid sequence having at least 80% sequence identity to SEQ ID NO: 1, 2, 4, 5, or 6, wherein the peptide is 15-30 amino acids in length;

(b) a peptide comprising an amino acid sequence having at least 95% sequence identity to SEQ ID NO: 3, wherein the peptide is 15-30 amino acids in length; or (c) a combination of the peptides of (a) and/or (b), wherein the peptide or the peptides in the combination further comprises a label.

8. The composition of claim 7, further comprising a pharmaceutically acceptable carrier.

9. The composition of claim 7, wherein the peptide comprises the amino acid sequence of SEQ ID NO: 1, 2, 3, 4, 5, or 6, or the combination of the peptides comprises two or more peptides, each peptide comprising the amino acid sequence of SEQ ID NO: 1, 2, 3, 4, 5, or 6.

10. The composition of claim 7, wherein the peptide comprises at least 5, 6, 7, 8, 9, 10, 11, 12, 13, 14, or 15 contiguous amino acids of the amino acid sequence of SEQ ID NO: 1, 2, 3, 4, 5, or 6.

11. The composition of claim 7, wherein the peptide is 15 amino acids in length.

12. The composition of claim 7, wherein the label is biotin, a fluorescent label, a chemiluminescent label, or a radioactive label.

* * * * *